(12) United States Patent
Vandyck et al.

(10) Patent No.: US 10,398,677 B2
(45) Date of Patent: Sep. 3, 2019

(54) N-PHENYL-CARBOXAMIDE DERIVATIVES AND THE USE THEREOF AS MEDICAMENTS FOR THE TREATMENT OF HEPATITIS B

(71) Applicant: JANSSEN SCIENCES IRELAND UC, Little Island, Co Cork (IE)

(72) Inventors: Koen Vandyck, Paal-Beringen (BE); Geerwin Yvonne Paul Haché, Kapellen (BE); Stefaan Julien Last, Lint (BE); Pierre Jean-Marie Bernard Raboisson, Rosieres (BE)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 0 days.

(21) Appl. No.: 15/886,766

(22) Filed: Feb. 1, 2018

(65) Prior Publication Data
US 2018/0153857 A1 Jun. 7, 2018

Related U.S. Application Data

(63) Continuation of application No. 14/782,308, filed as application No. PCT/EP2014/056601 on Apr. 2, 2014, now Pat. No. 9,895,349.

(30) Foreign Application Priority Data

Apr. 3, 2013 (EP) .................... 13162131

(51) Int. Cl.
| | | |
|---|---|---|
| C07D 207/16 | (2006.01) |
| C07D 207/48 | (2006.01) |
| A61K 31/40 | (2006.01) |
| C07D 405/12 | (2006.01) |
| C07D 409/12 | (2006.01) |
| C07D 487/08 | (2006.01) |
| C07D 209/42 | (2006.01) |
| A61K 31/4025 | (2006.01) |
| A61K 31/403 | (2006.01) |
| A61K 31/404 | (2006.01) |
| A61K 31/407 | (2006.01) |
| A61K 45/06 | (2006.01) |
| C07D 209/52 | (2006.01) |
| C07D 403/12 | (2006.01) |
| C07D 487/04 | (2006.01) |
| C07D 491/107 | (2006.01) |

(52) U.S. Cl.
CPC ............ *A61K 31/40* (2013.01); *A61K 31/403* (2013.01); *A61K 31/404* (2013.01); *A61K 31/407* (2013.01); *A61K 31/4025* (2013.01); *A61K 45/06* (2013.01); *C07D 207/16* (2013.01); *C07D 207/48* (2013.01); *C07D 209/42* (2013.01); *C07D 209/52* (2013.01); *C07D 403/12* (2013.01); *C07D 405/12* (2013.01); *C07D 409/12* (2013.01); *C07D 487/04* (2013.01); *C07D 487/08* (2013.01); *C07D 491/107* (2013.01)

(58) Field of Classification Search
CPC ........................... C07D 207/16; C07D 207/48
See application file for complete search history.

(56) References Cited

U.S. PATENT DOCUMENTS

| | | |
|---|---|---|
| 3,843,662 A | 10/1974 | Holland |
| 4,569,940 A | 2/1986 | Watts |
| 4,962,101 A | 10/1990 | DiNinno et al. |
| 4,995,898 A | 2/1991 | Nasu et al. |
| 5,272,167 A | 12/1993 | Ginjavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol et al. |
| 5,708,034 A | 1/1998 | Kleemann et al. |
| 5,723,411 A | 3/1998 | Stevenson |

(Continued)

FOREIGN PATENT DOCUMENTS

| | | |
|---|---|---|
| CA | 2950807 A1 | 12/2013 |
| CN | 1390201 A | 1/2003 |

(Continued)

OTHER PUBLICATIONS

Horig et al., et al., from bemnch to Clinic and back : Perspective on the 1st IQPC translational Research conference, Journal of translational medicine, Dec. 20, 2004, pp. 1-8, vol. 2 Issue 44.

(Continued)

*Primary Examiner* — Karen Cheng

(57) ABSTRACT

Inhibitors of HBV replication of Formula (I)

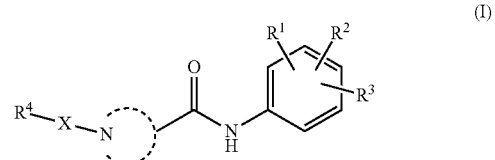

including stereochemically isomeric forms, and salts, hydrates, solvates thereof, wherein X, $R^1$, $R^2$, $R^3$ and $R^4$ have the meaning as defined herein.

The present invention also relates to processes for preparing said compounds, pharmaceutical compositions containing them and their use, alone or in combination with other HBV inhibitors, in HBV therapy.

13 Claims, No Drawings

(56) References Cited

U.S. PATENT DOCUMENTS

| | | |
|---|---|---|
| 5,756,524 A | 5/1998 | Riordan et al. |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin et al. |
| 6,025,367 A | 2/2000 | Forbes et al. |
| 6,265,408 B1 | 7/2001 | Forbes et al. |
| 6,476,025 B1 | 11/2002 | Gutterer |
| 6,650,463 B2 | 11/2003 | Obikawa et al. |
| 6,668,527 B2 | 12/2003 | Duplantier et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien |
| 7,384,967 B2 | 6/2008 | Polisetti et al. |
| 7,541,373 B2 | 6/2009 | Polisetti et al. |
| 7,544,700 B2 | 6/2009 | Halazy et al. |
| 7,576,688 B2 | 8/2009 | Lehtinen |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | DuBois et al. |
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |
| 8,071,779 B2 | 12/2011 | Lampe et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev |
| 8,207,195 B2 | 6/2012 | Navratil et al. |
| 8,227,489 B2 | 7/2012 | Dubois et al. |
| 8,273,754 B2 | 9/2012 | Ali et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,141 B2 | 4/2013 | Murata et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,808,702 B2 | 8/2014 | Reddy et al. |
| 8,889,716 B2 | 11/2014 | Prime et al. |
| 8,993,771 B2 | 3/2015 | Hartman |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil van Niel et al. |
| RE45,670 E | 9/2015 | Polisetti et al. |
| 9,156,839 B2 | 10/2015 | Vandyck et al. |
| 9,169,212 B2 | 10/2015 | Hartman et al. |
| 9,181,288 B2 | 11/2015 | Hartman et al. |
| 9,205,079 B2 | 12/2015 | Hartman |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 9,567,299 B2 | 2/2017 | Vandyck et al. |
| 9,579,313 B2 | 2/2017 | Hartman |
| 9,676,747 B2 | 6/2017 | Hartman et al. |
| 10,071,961 B2 | 9/2018 | Vandyck et al. |
| 2002/0049236 A1 | 4/2002 | Duplantier et al. |
| 2003/0114443 A1 | 6/2003 | Imamura et al. |
| 2004/0039009 A1 | 2/2004 | Jagtap et al. |
| 2004/0110802 A1 | 6/2004 | Thorarensen et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0221272 A1 | 10/2005 | Housman et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdoif et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0087415 A1 | 4/2010 | Whitten et al. |
| 2010/0113421 A1 | 5/2010 | Williams |
| 2010/0204210 A1 | 8/2010 | Sorensen |
| 2011/0009622 A1 | 1/2011 | Makoto et al. |
| 2011/0064695 A1 | 3/2011 | Qiu et al. |
| 2011/0064696 A1 | 3/2011 | Or et al. |
| 2011/0065686 A1 | 3/2011 | Mazola Reyes et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Navratil et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 8/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 | 4/2016 | Vandyck et al. |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334882 A1 | 11/2017 | Hartman et al. |

FOREIGN PATENT DOCUMENTS

| | | |
|---|---|---|
| CN | 101039919 A | 9/2007 |
| CN | 102093320 A | 6/2011 |
| CN | 102206172 A | 10/2011 |
| EP | 0232067 A2 | 8/1987 |
| EP | 0742200 A1 | 11/1996 |
| EP | 2280001 A4 | 1/2012 |
| JP | 62142164 | 6/1987 |
| JP | 2008179621 A | 7/2008 |

(56) References Cited

FOREIGN PATENT DOCUMENTS

| | | |
|---|---|---|
| JP | 2008525406 A | 7/2008 |
| JP | 2010535172 A | 11/2010 |
| WO | 198403281 A1 | 8/1984 |
| WO | 199207835 A1 | 5/1992 |
| WO | 1998023285 A1 | 6/1998 |
| WO | 199909022 A1 | 2/1999 |
| WO | 1999038845 A1 | 8/1999 |
| WO | 199948492 A1 | 9/1999 |
| WO | 199965906 A1 | 12/1999 |
| WO | 200105390 A2 | 1/2001 |
| WO | 200119788 A2 | 3/2001 |
| WO | 2001051487 A1 | 7/2001 |
| WO | 200155121 A1 | 8/2001 |
| WO | 200185694 A2 | 11/2001 |
| WO | 2002051410 | 7/2002 |
| WO | 2002064618 A2 | 8/2002 |
| WO | 2003002518 A1 | 1/2003 |
| WO | 2003007955 A2 | 1/2003 |
| WO | 2003044016 A1 | 5/2003 |
| WO | 2003101961 A1 | 12/2003 |
| WO | 2004010943 A2 | 2/2004 |
| WO | 2004011427 A2 | 2/2004 |
| WO | 2004022060 A2 | 3/2004 |
| WO | 2004058709 A2 | 7/2004 |
| WO | 2004086865 A1 | 10/2004 |
| WO | 2004099192 A2 | 11/2004 |
| WO | 2004100947 A2 | 11/2004 |
| WO | 2005016922 A1 | 2/2005 |
| WO | 2005044797 A1 | 5/2005 |
| WO | 2005087217 A1 | 9/2005 |
| WO | 2005105785 A2 | 11/2005 |
| WO | 2005115374 A1 | 12/2005 |
| WO | 2006002133 A1 | 1/2006 |
| WO | 2006012642 A2 | 2/2006 |
| WO | 2006024834 A1 | 3/2006 |
| WO | 2006053109 A1 | 5/2006 |
| WO | 2006067445 A2 | 6/2006 |
| WO | 2006067446 A1 | 6/2006 |
| WO | 2006123257 A2 | 11/2006 |
| WO | 2006128129 A2 | 11/2006 |
| WO | 2006128172 A2 | 11/2006 |
| WO | 2007031791 A1 | 3/2007 |
| WO | 2007070556 A2 | 6/2007 |
| WO | 2008011476 A2 | 1/2008 |
| WO | 2008022171 A1 | 2/2008 |
| WO | 2008054605 A | 5/2008 |
| WO | 2008093614 A1 | 8/2008 |
| WO | 2008137794 A1 | 11/2008 |
| WO | 2008154819 A1 | 12/2008 |
| WO | 2009016088 A1 | 2/2009 |
| WO | 2009018219 A2 | 2/2009 |
| WO | 2009062402 A1 | 5/2009 |
| WO | 2009086303 A2 | 7/2009 |
| WO | 2009131065 A1 | 10/2009 |
| WO | 2009146013 A1 | 12/2009 |
| WO | 2010018113 A2 | 2/2010 |
| WO | 2010043592 A1 | 4/2010 |
| WO | 2010059658 A1 | 5/2010 |
| WO | 2010088000 A2 | 8/2010 |
| WO | 2010123139 A1 | 10/2010 |
| WO | 2010138758 A1 | 12/2010 |
| WO | 2011002635 A1 | 1/2011 |
| WO | 2011035143 A2 | 3/2011 |
| WO | 2011088015 A1 | 7/2011 |
| WO | 2011088561 A1 | 7/2011 |
| WO | 2011109237 A1 | 9/2011 |
| WO | 2011112191 A1 | 9/2011 |
| WO | 2011123609 A1 | 10/2011 |
| WO | 2011140324 A1 | 11/2011 |
| WO | 2011155898 A1 | 12/2011 |
| WO | 2012016133 A2 | 2/2012 |
| WO | 2012018635 A2 | 2/2012 |
| WO | 2012033956 A1 | 3/2012 |
| WO | 2012049277 A1 | 4/2012 |
| WO | 2012075235 A1 | 6/2012 |
| WO | 2012080050 A1 | 6/2012 |
| WO | 2012117216 A1 | 9/2012 |
| WO | 2012136834 A1 | 10/2012 |
| WO | WO2013006394 A1 | 1/2013 |
| WO | 2013096744 A1 | 6/2013 |
| WO | 2013102655 A1 | 7/2013 |
| WO | 2013130703 A2 | 9/2013 |
| WO | 2013144129 A1 | 10/2013 |
| WO | 2013174962 | 11/2013 |
| WO | 2013181584 A2 | 12/2013 |
| WO | 2013184757 A1 | 12/2013 |
| WO | 2014033167 A1 | 3/2014 |
| WO | 2014033170 A1 | 3/2014 |
| WO | 2014033176 | 3/2014 |
| WO | 2014037480 A1 | 3/2014 |
| WO | 2014106019 A2 | 7/2014 |
| WO | 2014131847 A1 | 9/2014 |
| WO | 2014151958 A1 | 9/2014 |
| WO | 2014161888 A1 | 10/2014 |
| WO | 2014165128 A2 | 10/2014 |
| WO | 2014184328 A1 | 11/2014 |
| WO | 2014184350 A1 | 11/2014 |
| WO | 2014184365 A1 | 11/2014 |
| WO | 2014191301 A1 | 12/2014 |
| WO | 2014191726 A1 | 12/2014 |
| WO | 2014198880 A1 | 12/2014 |
| WO | 2015011281 A1 | 1/2015 |
| WO | 2015055764 A1 | 4/2015 |
| WO | 2015057945 A1 | 4/2015 |
| WO | 2015059212 A1 | 4/2015 |
| WO | 2015073774 A1 | 5/2015 |
| WO | 2015109130 A1 | 7/2015 |
| WO | 2015116923 A1 | 8/2015 |
| WO | 2015118057 A1 | 8/2015 |
| WO | 2015132276 A1 | 9/2015 |
| WO | 2015138895 A1 | 9/2015 |
| WO | 2015144093 A1 | 10/2015 |
| WO | 2015180631 A1 | 12/2015 |
| WO | 2016089990 A1 | 6/2016 |
| WO | 2016109663 A2 | 7/2016 |
| WO | 2016109684 A2 | 7/2016 |
| WO | 2016109689 A1 | 7/2016 |
| WO | 2016149581 A1 | 9/2016 |
| WO | 2016113273 A1 | 10/2016 |
| WO | 2016161268 A1 | 10/2016 |
| WO | 2016168619 A1 | 10/2016 |
| WO | 2016183266 A1 | 11/2016 |

OTHER PUBLICATIONS

Mohebbi, et al., An Overview of Hepatitis B Virus Surface Antigen Secreation Inhibitors, Frontier in Microbiology, 2018, pp. 1-9, vol. 9.
Schafer, et al., Failure Is option: learning from unsuccessful proof-ofconcepts trails, Drug Discovery Today, 2008, pp. 913-916, vol. 13 Issue 21/22.
Online Registry via STN Dec. 22, 2008, RN 1088200-12-7.
Online Registry via STN, Feb. 3, 2007, RN 924514-21-6.
Online Registry via STN, Feb. 9, 2003, RN 577752-12-6.
Bennes, et al., "Recognition-induced control and acceleration of a pyroole Diels-Alder reaction", Tetrahedron Letters, vol. 42 : pp. 2377-2380 (2001).
Berke, et al., "Capsid Assembly Modulator JNJ-56136379 Prevents de Novo Infection of Primary Human Hepatocytes with Hepatitis B Virus", Hepatology, Oct. 2016, pp. 124A, 234.
Brahmania, et al., "New Therapeutic Agents for Chronic Hepatitis B", Lancet Infec Dis, vol. 16: pp. e10-21 (Feb. 2016).
Brezillon, et al., "Antiviral Activity of Bay 41-4109 on Hepatitis B Virus in Humanized Alb-uPA/SCID Mice", PLos One, vol. 6 (12): pp. e25096 (1-6) (Dec. 2011).
Cai, et al., "Identification of disubstituted sulfonamide compounds as specific inhibitors of hepatitis B virus covalently closed circular DNA formation, Antimicrobial agents and chemotherapy", pp. vol. 56(8): pp. 4277-4288 (May 29, 2012).
Campagna et al., "Sulfamoylbenzamide Derivatives Inhibit the Assembly of Hepatitis B Virus Nucleocapsids", Journal of Virology, ),vol. 87 (12): pp. 6931-6942 (Jun. 2013).

(56) References Cited

OTHER PUBLICATIONS

Campagna, "Sulfamoylbenzamide Derivatives are a Novel Class of Hepatities B Virus Inhibitors Targeting PGRNA Encapsidation", 2011 International Meeting on Molecular Biology of Hepatitis B Viruses, Poster Presentation, (Oct. 3-12, 2011).
Carver, et al., Polyfunctionalisation of Imidazole via Sequential Imidazolyl Anion Formation, Tetrahedron, 1997, pp. 14481-14496, vol. 53 Issue 42.
Chang, et al., "NMR-spectroscopy-based Metabonomic Approach to the Analysis of Bay41-4109, a novel anti-HBV Compound, induced Hepatotoxicity in Rats", Toxicology Letters, vol. 173: pp. 161-167 (2007).
Cho, et al., "2-Amino-N-(2,6-dichloropyridin-3-yl)acetamide derivatives as a novel class of HBV capsid assembly inhibitor", Journal of Viral Hepatitis, vol. 21: pp. 843-852 (2014).
Cowie, et al., "Mortality due to viral hepatitis in the Global Burden of Disease Study 2010: new evidence of an urgent global public health priority demanding action", Antiviral Therapy,vol. 18: pp. 953-54 (2013).
Delaney, et al., "Phenylpropenamide Derivatives AT-61 and AT-130 Inhibit Replication of Wild-Tpe and Lamivudine-Resistant Strains of Hepatitis B Virus in Vitro", Antimicrobial Agents and Chemotherapy, vol. 46(9): pp. 3057-3060 (Sep. 2002).
Deres, et al., "Inhibition of Hepatitis B Virus Replication by Drug-Induced Depletion of Nucleocpsids", Science, vol. 299: pp. 893-896 (Feb. 7, 2003).
Duan, et al., 2-Phenylquinazolin-4(3H)-one, a class of potent PDE5 Inhibitors with High Selectivity Versus PDE6, Bioorganic & Medicinal Chemistry Letter, vol. 19: pp. 2777-2779 (2009).
El-Sayed, et al, "A Comparative Study of the 1-9 Reactions of Thiophene-2-Carboxanilides and related Compounds", Chemistry of Heterocyclic Compounds, vol. 34 (7): pp. 796-801 (Jan. 1, 1998).(XP000881506).
El-Sharief, et al., "Synthesis of Different Types of Chlorinated Sulphonamides with Expected Insecticidal and Bactericidal Activities", Proceedings of the Indian National Science Academy, vol. 53(1): pp. 179-188 (1987).
Ermann, et al., "Arylsulfonamide CB2 Receptor Agonists: SAR and Optimization of CB2 Selectivity", Bioorganic & Medicinal Chemistry Letters, vol. 18: pp. 1725-1729 (2008).
Foley, "An Effecient Synthesis of 2-Chloro-3-carboethoxy or 2-Chloro-3-cyano-4,5-disubstituted and 5-substituted Pyrroles", Tetrahedron Letters, vol. 35(33): pp. 5989-5992, (1994).
Gane, et al., "Phase 1a Safety and Pharmacokinetics of NVR3-778, a Potential First-in-class HBV Core Inhibitor", The Abstract of the Liver Meeting 2014 (AASLD), Abstract LB-19, Boston, MA (2014).
Gang Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.
Geies, et al., Synthesis of some Thiazolo[3,2-a]Pyrimidines, Phosphorus, Sulfur and Silicon, vol. 56: pp. 87-93 (1991).
Geng et al., "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.
Goodman, et al, "Discovery of potent, selective sulfonylfuran urea endothelial lipase inhibitors", Bioorganic & Medicinal Chemistry Letters, vol. 19:pp. 27-30 (2009).
Guo et al., "HBc binds to the CpG island of HBV cccDNA and promotes an epigenetic permissive state", Epigenetics, vol. 6 (6): pp. 720-726 (Jun. 2011).
Hogan, et al., "Aqueous Process Chemistry: The Preparation of Aryl Sulfonyl Chlorides", Organic Process Research & Development, vol. 13: pp. 875-879 (2009).
Huang, et al., "Blockage of HBV Virus Replication and Inhibition of cccDNA Establishment by Core Protein Allosteric Modifiers (CpAMs)", Hepatology, vol. 64 (1 Suppl): pp. 937A-938A, ( Oct. 2016).

Hughes, et al., "Hepatitis Delta Virus", The Lancet, vol. 378: pp. 73-85, (Jul. 2, 2011).
Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).
Katen, et al., "Assembly-Directed Antivirals Differentially Bind Quasiequivalend Pockets to Modify Hepatitis B Virus Capsid Tertiary and Quaternary Structure", Structure, vol. 21: pp. 1406-1416 (Aug. 6, 2013).
Kim, et al, "Discovery of novel HCV polymerase inhibitors using pharmacophore-based virtual screening", Bioorganic & Medicinal Chemistry Letters, vol. 21 (11): pp. 3329-3334 (Apr. 4, 2011). (XP028211474).
Klumpp, et al., "High Antiviral Activity of the HBV Core Inhibitor NVR 3-778 in the Humanized UPA/SCID Mouse Model", Journal of Hepatology, vol. 62:p. S235 (2015).
Klumpp, et al., "High-resolution crystal structure of a hepatitis B virus replication inhibitor bound to the viral core protein", PNAS, vol. 112(49): pp. 15196-15201 (Dec. 8, 2015).
Lam, et al., "HBV Corre Assembly Modulators Block Antigen Prouction When Present During Infection, but not during Persistent Infection", The Abstracts of the Liver Meeting 2016 (AASLD), vol. 64 (1 Suppl.), Boston, MA (Oct. 2016).
Lam, et al., "Inhibition of Hepatitis B Virus Replication by the HBV Core Inhibitors NVR3-778", The Abstract of the Liver Meeting 2015 (AASLD), Abstract 33: p. 223A, San Francisco, CA (Oct. 2015).
Lam, et al., "Serum HBV RNA as a Pharmacodynamic (PD) Marker of HBV Treatment Response to Core Assembly Modulator NVR 3-778 and Pegylate-Interferon Alpha", Poster Presented in the AASLD/EASL—HBV Treatment Endpoints Workshop, Poster No. 3774, Alexandria, VA (Sep. 9, 2016).
Lambeng, et al, "Arylsulfonamides as a new class of cannabinoid CB1 receptor ligands:identification of a lead and initial SAR studies", Bioorganic & Medicinal Chemistry Letters, vol. 17(1) pp. 272-277 (Dec. 22, 2006).
Lau, et al., "Peginterferon Alfa-2a, Lamivudine, and the Combination for HBeAg-Positive Chronic Hepatitis B", New England Journal of Medicine, vol. 352(26): pp. 2682-2695 (Jun. 30, 2005).
Li Bing, et al., Progress in anti Hepatitus B Virus non-nucleosidic drugs, J. Liaoning Medical University, vol. 30(1): pp. 88-91 (Dec. 31, 2009.
Liaw, et al., "Hepatitis B Virus Infection", Lancet, vol. 373: pp. 582-592 (Feb. 14, 2009).
Lucifora, et al., "Specific and Nonhepatotoxic Degradation of Nuclear Hepatitis B Virus cccDNA", Science, vol. 343: pp. 1221-1228 (Mar. 14, 2014).
Mabrouk, "Discovering best candidates for Hepatocellular Carcinoma (HCC) by in-silico techniques and tools", Int. J. Bioinformatics Research and Applications, vol. 8 (1/2): pp. 141-152 (Jan. 1, 2012).
Manzoor, et al., "Hepatitis B Virus Therapy: What's the future holding for us?", World Journal of Gastroenterology, vol. 21(44): pp. 12558-12575 (Nov. 28, 2015).
Marcellin, et al., "Peginterferon Alfa-2a Alone, Lamivudine Alone, and the Two in Combination in Patients with HBeAg-Negative Chronic Hepatitis B", The New England Journal of Medicine, vol. 351(12): pp. 1206-1217 (Sep. 16, 2014).
Mohamed, et al., "Synthesis of Different Types of Chlorinated Sulphonamides with Expected Insecticidal and Antimicrobial Activities", Acta Pharmaceutica Jugoslavica, vol. 36 (3): pp. 301-310, (1986).
Online Registr via STN, Dec. 28, 2008, RN 1090750-88-1.
Online Registry via STN , Aug. 13, 2012, RN 1390589-54-4.
Online Registry via STN Feb. 2, 2007, RN 919040-39-4.
Online Registry via STN Feb. 2, 2007, RN 919040-53-2.
Online Registry via STN Feb. 2, 2007, RN 919040-55-4.
Online Registry via STN Jun. 8, 2012. RN 1386725-02-5.
Online Registry via STN Jul. 6, 2012, RN 1375909-37-7.
Online Registry via STN Aug. 12, 2012, RN 1389720-57-3.
Online Registry via STN Oct. 10, 2001, RN 361373-90-2.
Online Registry via STN Nov. 12, 2007, RN 957487-45-5.

(56) References Cited

OTHER PUBLICATIONS

Online Registry via STN Nov. 12, 2007, RN 957487-49-9.
Online Registry via STN Dec. 8, 2012, RN 1389686-79-6.
Online Registry via STN Aug. 13, 2012, RN 1390500-09-0.
Online Registry via STN Jan. 16, 2001, RN 314043-17-9.
Online Registry via STN Jan. 17, 2013, RN 1424462-66-7.
Online Registry via STN Sep. 18, 2012, RN 1394742-82-5.
Online Registry via STN 2010, RN 1253220-91-5.
Online Registry via STN Aug. 30, 2011, RN 1325664-90-1.
Online Registry via STN, Jan. 24, 2008, RN 296790-26-6.
Online Registry via STN, Feb. 2, 2007, RN 9019040-48-5.
Online Registry via STN, Feb. 2, 2007, RN 919040-37-2.
Online Registry via STN, Jun. 5, 2011, RN 1291044-81-9.
Online Registry via STN, Jun. 9, 2011, RN 1328738-57-3.
Online Registry via STN, Jul. 10, 2008, RN 1057788-44-9.
Online Registry via STN, Jul. 10, 2008, RN 1057871-39-2.
Online Registry via STN, Sep. 1, 2001, RN 313253-89-3.
Online Registry via STN, Oct. 3, 2010, RN 1208400-27-4.
Online Registry via STN, Feb. 15, 2007, RN 921179-95-5.
Online Registry via STN, Aug. 15, 2011, RN 1317923-24-2.
Online Registry via STN, Aug. 15, 2011, RN 1318022-74-0.
Online Registry via STN, Mar. 17, 2003, RN 499189-09-2.
Online Registry via STN, May 18, 2011, RN 1296380-95-4.
Online Registry via STN, Oct. 18, 2000, RN 296894-70-7.
Online Registry via STN, Sep. 20, 2013, RN 1452780-00-5.
Online Registry via STN, Apr. 24, 2002, RN 406926-60-1.
Online Registry via STN, Apr. 28, 2011, RN 1286906-97-5.
Online Registry via STN, Apr. 19, 2008, RN 930914-71-9.
Patani, et al., "Bioisoterism: A rational Approach in Drug Design", Chem. Rev., vol. 96: pp. 3147-3176 (1996).
Patel, et al., "Synthesis N-Ethylpiperazinyl Sulfonyl Group Incorporated Benzamides", Indian Journal of Heterocyclic Chemistry, vol. 15: pp. 201-202 (Oct.-Dec. 2005).
Qidong You et al, Pharmaceutical Chemistry, Chemical Industry Press, Jan. 31, 2014, pp. 32-33, /.
Qiu, et al, "Antihepatitis B therapy: a review of current medications and novel small molecule inhibitors", Fudamental & Clinical Pharmacology, pp. 1-18 (XP055105340) (Nov. 1, 2013).
Qiu, et al., "Design and Synthesis of Orally Bioavailable 4-Methyl Heteroaryldihydropyrimidine Based Hepatitis B Virus (HBV) Capsid Inhibitors", Journal of Medicinal Chemistry, vol. 59: pp. 7651-7666, (2016).
Schroder, et al., "Arzneimittelchemie Passage", Arzneimittelchemei Grundlagen Nerven Musklen and Gewebe Gewebe, vol. XX (XX): pp. 30-33 (Jan. 1, 1976).
Shi, et al., "NMR-spectroscopy-based metanonomic approach to the analysis of Bay41-4109, a novel anti-HBV compound, induced hepatotoxcity in rats", Toxicology Letters, vol. 173: pp. 161-167 (2007).
Stalder, et al, "Selective antagonists of mouse trace amine-associated receptor 1 (mTAAR1): Discovery of EPPTB (RO5212773)", Bioorganic & Medicinal Chemistry Letters, vol. 21: pp. 1227-1231 (Dec. 21, 2010).
Stray, et al., "A Heteroaryldihydropyrimidine Activates and Can Misdirect Hepatitis B Virus Capsid Assembly", PNAS, vol. 102(23): pp. 8138-8143 (Jun. 7, 2005).
Stray, et al., "Bay 41/4109 has multiple effects on Hepatitis B virus capsid assembly", Journal of Molecular Recognition, vol. 19: pp. 542-548 (2006).

Tan, et al., Genetically Altering the Thermodynamics and Kinetics of Hepatitis B Virus Capsid Assembly has Profound Effects on Virus Replication in Cell Culture, Journal of Virology, vol. 87(6): pp. 3208-3216 (Mar. 2013).
Taylor, et al., "A Brain-Permeable Small Molecule Reduces Neuronal Cholesterol by Inhibiting Activity of Sirtuin 2 Deacetylase", ASC Chemical Biology, vol. 6: pp. 540-546 (2011).
The Merk Index "Infliximab", An Encyclopedia of Chemicals, Drugs and Biologicals, 14th Ed., p. 924 (2013).
The Merk Index, "Zidovudine", An Encyclopedia of Chemicals, Drugs and Biologicals, 14th Ed., p. 1885 (2013).
Thompson et al., "Toll-like receptors, RIG-I-like RNA Helicases and the Antiviral Innate Immune Response", Immunology and Cell Biology, vol. 85: pp. 435-445 (2007).
Wang et al., "In vitro inhibition of HBV replication by a novel compound, GLS4, and its efficacy against adefovir-dipovoxil-resistant HBV mutations", Antiviral Therapy, vol. 17:pp. 793-803 (2012).
Wang, et al., "Serum hepatitis B virus RNS is encapsidated pregenome RNA that may be associated with persistence of viral infection and rebound", Journal of Hepatology, vol. 65: pp. 700-710(2016).
Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Watanabe, et al, "Ortho lithiation of N,N-dimethylbenzenesulfunamide by n-butyllithium. Condensation with electrophilic compounds", Candian Journal of Chemistry, vol. 47: pp. 1543-1546 (Oct. 30, 1968).
Weber et al., "Inhibition of Human Hepatitis B Virus (HBV) by a Novel Non-Nucleosidic Compound in a Transgenic Mouse Model", Antiviral Research, vol. 54: pp. 69-78 (2002).
West, "Chapter 10 Solid Solutions", Solid State Chemistry and Its Applications, John Wiley & Sons, pp. 33-36 (1984).
Wu, et al., "Preclinical Characterization of GLS4, an Inhibitor of Hepatitis B Virus Core Particle Assembly", Antimicrobial Agents and Chemotherapy, vol. 57(11): pp. 5344-5354 (Nov. 2013).
Yang, et al., "Effects of a Hepatitis B Virus Inhibitor, NZ-4, on Capsid Formation", Antiviral Research, vol. 125: pp. 25-33 (2016).
Yang, et al., "Isothiafludine, a novel non-nucleoside compound inhibits hepatitis B virus replication through blocking pregenomic RNA encapsidation", Acta Pharmacologica Sinica, vol. 35: pp. 410-418 (2014).
Yarmolchuk et al., "Synthesis of beta-fluoro-beta-proline", Tetrahedron Letters, vol. 52: pp. 1300-1302, (2011).
Yogaratnam, et al., "Safety, Tolerability and Pharmacokentics of JNJ 56136379, a Novel HBV Capsid Assembly Modulator in Healthy Subjects", The Abstracts of the Liver Meeting 2016 (AASLD), Abstract 1881: pp. 930A-931A, Boston, MA (Oct. 2016).
Yuen, et al., "ARC-520 Produces Deep and Durable Knockdown of Viral Antigen and DNA in Phase II Study in Patients with Chronic Hepatitis B", The Abstracts of the Liver Meeting 2015, Abstract LB-10, pp. 1385A-1386A, San Francisco, CA (Oct. 2015).
Yuen, et al., "NVR 3-778, a first-in-class HBV core inhibitor, alone and in combination with PEG-Interferon (PEGIFN), In treatment-naive HBEAG-positive patients: early reductions in HBV DNA and HBEAG", The Abstracts of the International Liver Congress (EASL), Abstract LB-06: pp. S210-S211 (Oct. 2016).
Zhang, et al., "A Potent Small Molecule Inhibits Polyglutamine Aggregation in Huntington's Disease Neurons and Suppresses Neurodegeneration in Vivo", PNAS, vol. 102 (3): pp. 892-897 (2005).
Zlotnick, et al., "Core Protein: A pleiotropic Keystone in the HBV Lifecycle", Antiviral Research, vol. 121: pp. 32-93 (2015).
Zoulim, et al., "Current Treatments for Chronic Hepatitis B Virus Infections", Current Opinion in Virology, vol. 18: pp. 109-116 (2016).
Online Registry Via STN 03.02.2012, RN 1359583-56-4.
Online Registry Via STN 03.02.2012, RN 1359596_55_6.

N-PHENYL-CARBOXAMIDE DERIVATIVES AND THE USE THEREOF AS MEDICAMENTS FOR THE TREATMENT OF HEPATITIS B

CROSS-REFERENCE TO RELATED APPLICATIONS

This application is a continuation of U.S. patent application Ser. No. 14/782,308 filed on Oct. 2, 2015, which is a national phase entry of International Application No. PCT/EP2014/056601, filed on Apr. 2, 2014, which claims priority to EP Patent Application No. 13162131.0, filed Apr. 3, 2013, each of which is incorporated herein in its entirety.

BACKGROUND ART

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China. HBV has infected approximately 2 billion people worldwide of which approximately 350 million people have developed chronic infections. The virus causes the disease hepatitis B and chronic infection is correlated with a strongly increased risk for the development cirrhosis and hepatocellular carcinoma.

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine.

In addition, heteroaryldihydropyrimidines (HAPs) were identified as a class of HBV inhibitors in tissue culture and animal models (Weber et al., Antiviral Res. 54: 69-78).

WO/2013/006394, published on Jan. 10, 2013, relates to a subclass of Sulphamoyl-arylamides active against HBV.

Amongst the problems which HBV direct antivirals may encounter are toxicity, mutagenicity, lack of selectivity, poor efficacy, poor bioavailability, and difficulty of synthesis.

There is a need for additional HBV inhibitors that may overcome at least one of these disadvantages or that have additional advantages such as increased potency or an increased safety window.

DESCRIPTION OF THE INVENTION

The present invention relates to a compound of Formula (I)

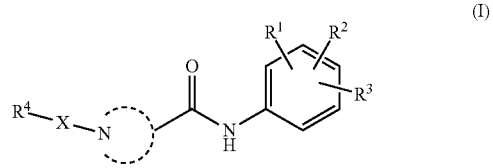

or a stereoisomer or tautomeric form thereof, wherein:

represents:

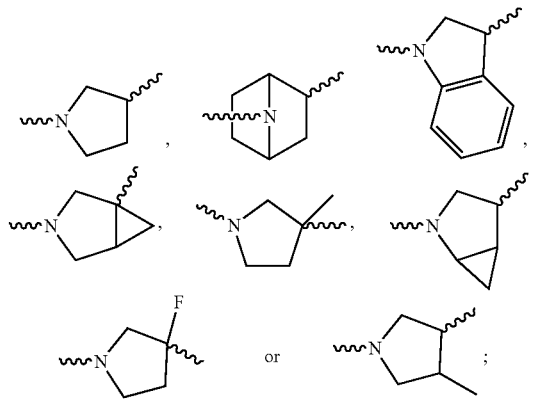

X represents —($SO_2$)— or a single bond, wherein,
When X represents —($SO_2$)—:
  $R^4$ is selected from the group consisting of —$NR^5R^6$, $C_1$-$C_6$alkyl, and a 3-7 membered saturated ring optionally containing one or more heteroatoms each independently selected from the group consisting of O, S and N, such 3-7 membered saturated ring or $C_1$-$C_6$alkyl optionally being substituted with one or more substituents each independently selected from the group consisting of hydrogen, fluoro, $C_1$-$C_4$alkyloxy, OH, oxo, $C_1$-$C_4$alkyl, and cyclopropyl,
  and $R^1$, $R^2$ and $R^3$ are independently selected from the group consisting of Hydrogen, Halogen, CN, Chloro, $CHF_2$, $CH_2F$, $CF_3$ and $C_1$-$C_3$alkyl and cyclopropyl;
When X represents a single bond:
  $R^4$ is —C(=O)O—$R^7$,
  and $R^1$, $R^2$ and $R^3$ are independently selected from the group consisting of Hydrogen, Halogen, CN, Chloro, $CHF_2$, $CH_2F$, $CF_3$ and $C_1$-$C_3$alkyl and cyclopropyl; such that at least one of $R^1$, $R^2$ and $R^3$ is Fluor, and one other of $R^1$, $R^2$ and $R^3$ is Hydrogen, Halogen, CN, Chloro, $CHF_2$, $CH_2F$, $CF_3$ and $C_1$-$C_3$alkyl and cyclopropyl;
$R^5$ is selected from the group consisting of Hydrogen or methyl;
$R^6$ is selected from the group consisting of $C_1$-$C_6$alkyl or a 3-7 membered saturated ring optionally containing one or more heteroatoms each independently selected from the group consisting of O, S and N, such 3-7 membered saturated ring or $C_1$-$C_6$alkyl optionally being substituted with one or more substituents each independently selected from the group consisting of hydrogen, fluoro, CN, OH, oxo, —NHC(=O)O—C$_1$-C$_4$alkyl, C$_1$-C$_4$alkyl optionally substituted with R$^8$, C$_1$-C$_4$alkyloxy,

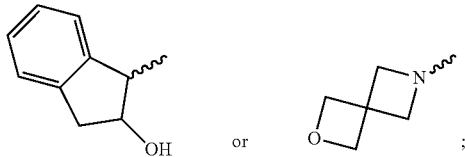

R$^7$ is selected from the group consisting of C$_1$-C$_6$alkyl or a 3-7 membered saturated ring optionally containing one or more heteroatoms each independently selected from the group consisting of O, S and N;
R$^8$ is selected from the group consisting hydrogen, OH, C$_1$-C$_4$alkyl or CN;
or a pharmaceutically acceptable salt or a solvate thereof.

The invention further relates to a pharmaceutical composition comprising a compound of Formula (I), and a pharmaceutically acceptable carrier.

The invention also relates to the compounds of Formula (I) for use as a medicament, preferably for use in the prevention or treatment of an HBV infection in a mammal.

In a further aspect, the invention relates to a combination of a compound of Formula (I), and another HBV inhibitor.

DEFINITIONS

The term "C$_{1-3}$alkyl" as a group or part of a group refers to a hydrocarbyl radical of Formula C$_n$H$_{2n+1}$ wherein n is a number ranging from 1 to 3. In case C$_{1-3}$alkyl is coupled to a further radical, it refers to a Formula C$_n$H$_{2n}$. C$_{1-3}$alkyl groups comprise from 1 to 3 carbon atoms, more preferably 1 to 2 carbon atoms. C$_{1-3}$alkyl includes all linear, or branched alkyl groups with between 1 and 3 carbon atoms, and thus includes such as for example methyl, ethyl, n-propyl, and i-propyl.

C$_{1-4}$alkyl as a group or part of a group defines straight or branched chain saturated hydrocarbon radicals having from 1 to 4 carbon atoms such as the group defined for C$_{1-3}$alkyl and butyl and the like.

C$_{1-6}$alkyl as a group or part of a group defines straight or branched chain saturated hydrocarbon radicals having from 1 to 6 carbon atoms such as the groups defined for C$_{1-4}$alkyl and pentyl, hexyl, 2-methylbutyl and the like.

The term "C$_{1-3}$alkyloxy" as a group or part of a group refers to a radical having the Formula —OR$^c$ wherein R$^c$ is C$_{1-3}$alkyl. Non-limiting examples of suitable C$_{1-3}$alkyloxy include methyloxy (also methoxy), ethyloxy (also ethoxy), propyloxy and isopropyloxy.

The term oxo, C(=O), or carbonyl refers to a group composed of a carbon atom double bonded to an oxygen atom.

As used herein, the term "3-7 membered saturated ring" means saturated cyclic hydrocarbon with 3, 4, 5, 6 or 7 carbon atoms and is generic to cyclopropyl, cyclobutyl, cyclopentyl, cyclohexyl and cycloheptyl.

Such saturated ring optionally contains one or more heteroatoms, such that at least one carbon atom is replaced by a heteroatom selected from N, O and S, in particular from N and O. Examples include oxetane, tetrahydro-2H-pyranyl, piperidinyl, tetrahydrofuranyl, morpholinyl, thiolane 1,1-dioxide and pyrrolidinyl. Preferred are saturated cyclic hydrocarbon with 3 or 4 carbon atoms and 1 oxygen atom. Examples include oxetane, and tetrahydrofuranyl.

It should be noted that different isomers of the various heterocycles may exist within the definitions as used throughout the specification. For example, pyrrolyl may be 1H-pyrrolyl or 2H-pyrrolyl.

The term halo and halogen are generic to fluoro, chloro, bromo or iodo. Preferred halogens are fluoro and chloro.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

Positions indicated on phenyl (e.g. ortho, meta and/or para) are indicated relative to the bond connecting the phenyl to the main structure. An example with regard to the position of R$^1$, any location is indicated relative to the nitrogen (*) connected to the main structure:

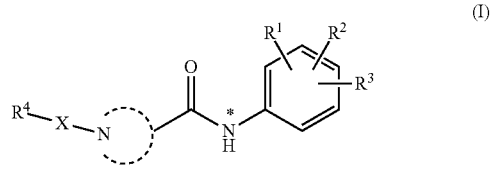

(I)

When any variable (e.g. halogen or C$_{1-4}$alkyl) occurs more than one time in any constituent, each definition is independent.

For therapeutic use, the salts of the compounds of formula (I) are those wherein the counter ion is pharmaceutically or physiologically acceptable. However, salts having a pharmaceutically unacceptable counter ion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids;
or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric forms of formula (I) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

DETAILED DESCRIPTION OF THE INVENTION

Whenever used hereinafter, the term "compounds of formula (I)",

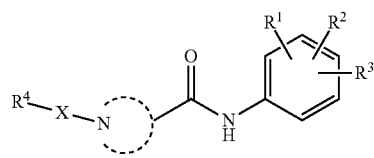

or "the present compounds" or similar term is meant to include the compounds of general formula (I),(Ib), salts, stereoisomeric forms and racemic mixtures or any subgroups thereof. Compounds for use in the prevention or treatment of an HBV infection in a mammal are disclosed as compounds per se and not limited to this use unless restricted by the claims.

In a first aspect, the invention provides compound of Formula (I)

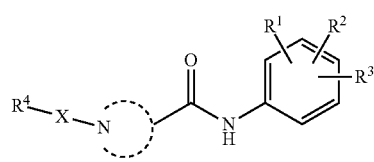

or a stereoisomer or tautomeric form thereof, wherein:

represents:

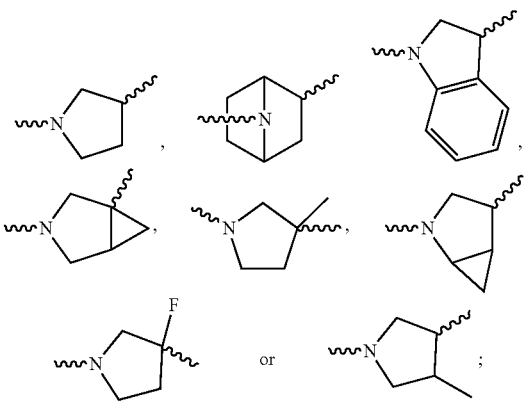

X represents —(SO$_2$)— or a single bond, wherein,
When X represents —(SO$_2$)—:
$R^4$ is selected from the group consisting of —NR$^5$R$^6$, C$_1$-C$_6$alkyl, and a 3-7 membered saturated ring optionally containing one or more heteroatoms each independently selected from the group consisting of O, S and N, such 3-7 membered saturated ring or C$_1$-C$_6$alkyl optionally being substituted with one or more substituents each independently selected from the group consisting of hydrogen, fluoro, C$_1$-C$_4$alkyloxy, OH, oxo, C$_1$-C$_4$alkyl, and cyclopropyl,
and R$^1$, R$^2$ and R$^3$ are independently selected from the group consisting of Hydrogen, Halogen, CN, Chloro, CHF$_2$, CH$_2$F, CF$_3$ and C$_1$-C$_3$alkyl and cyclopropyl;

When X represents a single bond:

R⁴ is —C(=O)O—R⁷, and R¹, R² and R³ are independently selected from the group consisting of Hydrogen, Halogen, CN, Chloro, CHF₂, CH₂F, CF₃ and C₁-C₃alkyl and cyclopropyl; such that at least one of R¹, R² and R³ is Fluor, and one other of R¹, R² and R³ is Hydrogen, Halogen, CN, Chloro, CHF₂, CH₂F, CF₃ and C₁-C₃alkyl and cyclopropyl;

R⁵ is selected from the group consisting of Hydrogen or methyl;

R⁶ is selected from the group consisting of C₁-C₆alkyl or a 3-7 membered saturated ring optionally containing one or more heteroatoms each independently selected from the group consisting of O, S and N, such 3-7 membered saturated ring or C₁-C₆alkyl optionally being substituted with one or more substituents each independently selected from the group consisting of hydrogen, fluoro, CN, OH, oxo, —NHC(=O)O—C₁-C₄alkyl, C₁-C₄alkyl optionally substituted with R⁸, C₁-C₄alkyloxy,

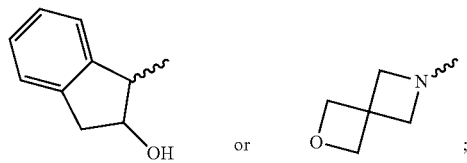

R⁷ is selected from the group consisting of C₁-C₆alkyl or a 3-7 membered saturated ring optionally containing one or more heteroatoms each independently selected from the group consisting of O, S and N;

R⁸ is selected from the group consisting hydrogen, OH, C₁-C₄alkyl or CN;

or a pharmaceutically acceptable salt or a solvate thereof.

In a further aspect, the invention relates to compounds of Formula (I)

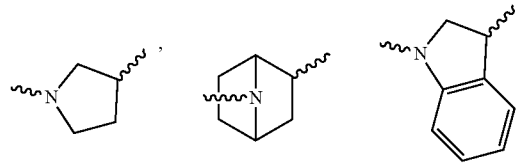

or a stereoisomer or tautomeric form thereof, wherein:

represents:

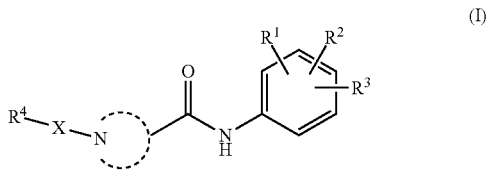

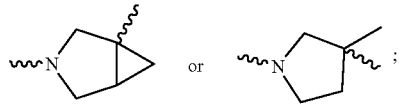

X represents —(SO₂)— or a single bond wherein,

When X represents —(SO₂)—,

R⁴ is selected from the group consisting of —NR⁵R⁶, C₁-C₆alkyl, and a 3-7 membered saturated ring optionally containing one or more heteroatoms each independently selected from the group consisting of O, S and N, such 3-7 membered saturated ring or C₁-C₆alkyl optionally being substituted with one or more substituents each independently selected from the group consisting of hydrogen, fluoro, C₁-C₄alkyloxy, OH, oxo, C₁-C₄alkyl, and cyclopropyl, and R¹, R² and R³ are independently selected from the group consisting of Hydrogen, Fluor, Chloro, CHF₂, CH₂F, CF₃ and methyl;

When X represents a single bond:

R⁴ is —C(=O)O—R⁷, and R¹, R² and R³ are independently selected from the group consisting of Hydrogen, Fluor, Chloro, CHF₂, CH₂F, CF₃ and methyl, such that at least one of R¹, R² and R³ is Fluor, and one other of R¹, R² and R³ is Fluor, CHF₂, CH₂F, CF₃ or methyl.

R⁵ is selected from the group consisting of Hydrogen or methyl;

R⁶ is selected from the group consisting of C₁-C₆alkyl or a 3-7 membered saturated ring optionally containing one or more heteroatoms each independently selected from the group consisting of O, S and N, such 3-7 membered saturated ring or C₁-C₆alkyl optionally being substituted with one or more substituents each independently selected from the group consisting of hydrogen, or C₁-C₄alkyl;

R⁷ is selected from the group consisting of C₁-C₆alkyl or a 3-7 membered saturated ring optionally containing one or more heteroatoms each independently selected from the group consisting of O, S and N;

or a pharmaceutically acceptable salt or a solvate thereof.

In one embodiment of the present invention,

represents

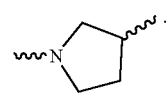

In a further embodiment of the present invention, compounds are represented by Formula (Ib)

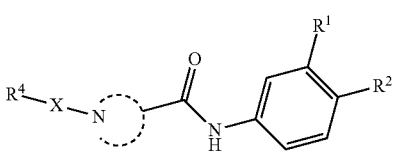

or a stereoisomer or tautomeric form, or pharmaceutically acceptable salts or a solvate thereof.

In a preferred embodiment, compounds of Formula (I) or (Ib) are envisioned wherein $R^1$ is selected from either Fluor or methyl, and $R^2$ is Fluor.

In yet another embodiment, compounds of Formula (I) or (Ib) are envisioned wherein X is —$(SO_2)$—, $R^4$ is $NR^5R^6$ and $R^5$ and $R^6$ are as defined above.

In a further embodiment, compounds of Formula (I) or (Ib) are envisioned wherein $R^4$ contains a 3-7 membered saturated ring optionally containing one oxygen.

Another embodiment of the present invention relates to those compounds of formula (I) or any subgroup thereof as mentioned in any of the other embodiments wherein one or more of the following restriction applies:

(a) $R^6$ is $C_1$-$C_6$alkyl optionally being substituted with one or more Fluoro.
(b) $R^1$ is methyl.
(c) $R^2$ and $R^3$ are independently selected from the group consisting of Hydrogen, Fluoro and methyl.
(d) $R^6$ contains a 3-7 membered saturated ring optionally containing one oxygen, more specifically $R^6$ is a 4 or 5 membered saturated ring containing one oxygen, such 4 or 5 membered saturated ring optionally substituted with methyl.
(e) $R^6$ comprises a branched $C_3$-$C_6$alkyl optionally substituted with one or more Fluoro, or $R^6$ comprises a $C_3$-$C_6$cycloalkyl wherein such $C_3$-$C_6$cycloalkyl is substituted with one or more Fluoro or substituted with $C_1$-$C_4$ substituted with one or more Fluoro. More specifically, $R^6$ is a branched $C_3$-$C_6$alkyl substituted with one or more Fluoro.
(f) $R^6$ is selected from the group consisting of $C_2$-$C_6$alkyl optionally being substituted with one or more Fluoro.

Further combinations of any of the sub- or preferred embodiments are also envisioned to be in the scope of the present invention.

Preferred compounds according to the invention are compound or a stereoisomer or tautomeric form thereof with a formula selected from table 1.

In a further aspect, the present invention concerns a pharmaceutical composition comprising a therapeutically or prophylactically effective amount of a compound of Formula (I) as specified herein, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of Formula (I), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of Formula (I) are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma.

Due to their antiviral properties, particularly their anti-HBV properties, the compounds of Formula (I) or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular human, infected by HBV, or being at risk of infection by HBV, said method comprising the administration of a therapeutically effective amount of a compound of Formula (I).

The compounds of Formula (I), as specified herein, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection.

The present invention also relates to the use of the present compounds in the manufacture of a medicament for the treatment or the prevention of HBV infection.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of formula (I) or any subgroup thereof, as specified herein with other anti-HBV agents. The term "combination" may relate to a product or kit containing (a) a compound of Formula (I), as specified above, and (b) at least one other compound capable of treating HBV infection (herein designated as anti-HBV agent), as a combined preparation for simultaneous, separate or sequential use in treatment of HBV infections. In an embodiment, the invention concerns combination of a compound of formula (I) or any subgroup thereof with at least one anti-HBV agent. In a particular embodiment, the invention concerns combination of a compound of formula (I) or any subgroup thereof with at least two anti-HBV agents. In a particular embodiment, the invention concerns combination of a compound of formula (I) or any subgroup thereof with at least three anti-HBV agents. In a particular embodiment, the invention concerns combination of a compound of formula (I) or any subgroup thereof with at least four anti-HBV agents.

The combination of previously known anti-HBV agents, such as interferon-α (IFN-α), pegylated interferon-α, 3TC, adefovir or a combination thereof, and, a compound of formula (I) or any subgroup thereof can be used as a medicine in a combination therapy.

Generic Synthesis:

The substituents represented in this general synthesis section are meant to include any substituent or reactive species that is suitable for transformation into any substituent according to the present invention without undue burden for the person skilled in the art.

The general synthesis of compound of Formula (I) is described in scheme 1 and scheme 2. As described in scheme 1, an amino acid of general Formula (II) is reacted with a reagent of general formula $R^4$—X—Y, examples of such reagents with general formula $R^4$—X—Y, in the context of scheme 1, are, but are not limited to, ClC(=O)O—$R^7$,

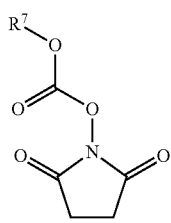

and $R^4SO_2C_1$, in the presence of a base like for example DIPEA. The resulting carboxylic acid III is reacted with an aniline of general formula (IV), for example under typical amide formation conditions like for example under the influence of HATU and DIPEA in $CH_2Cl_2$ at room temperature, resulting in compounds of general Formula (I).

Scheme 1

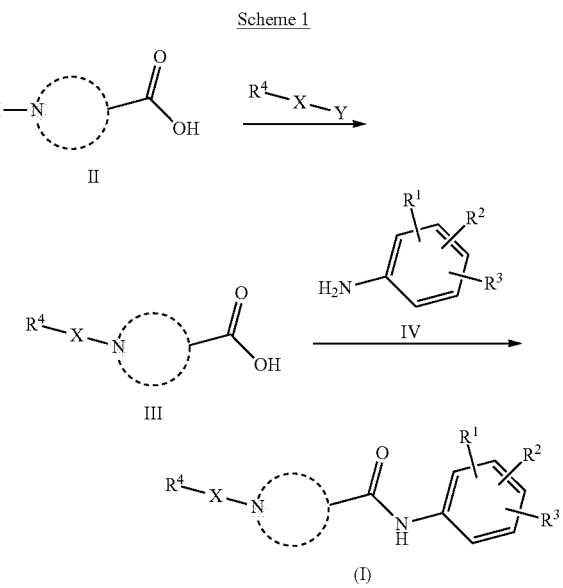

Another possible synthetic route to compounds of general Formula (I) is described in scheme 2. In this case, compound V, an amino acid with a protection group PG on nitrogen, where PG for example can be Boc (tert-Butoxy)carbonyl) or Cbz (Benzyloxycarbonyl), is reacted with an aniline compound of general Formula (IV), under typical amide formation conditions, like for example under the influence of HATU and DIPEA in $CH_2Cl_2$. The resulting compound of general formula VI is deprotected, for example by treatment with HCl in iPrOH/$CH_2Cl_2$ or TFA in $CH_2Cl_2$ in case PG equals Boc, resulting in a compound of general formula VII. Further reaction of compound of general VII with a reagents of general formula $R_4$—X—Y (examples of $R_4$—X—Y in the context of scheme 2, are, but are not limited to, ClC(=O)O—$R^7$, $R_4SO_2Cl$ and

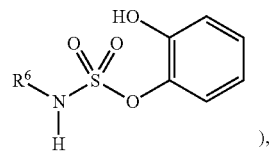

), possibly in the presence of a base like for example $NEt_3$, results in compounds of general Formula (I).

Scheme 2

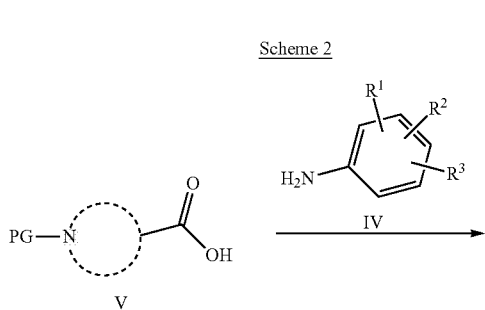

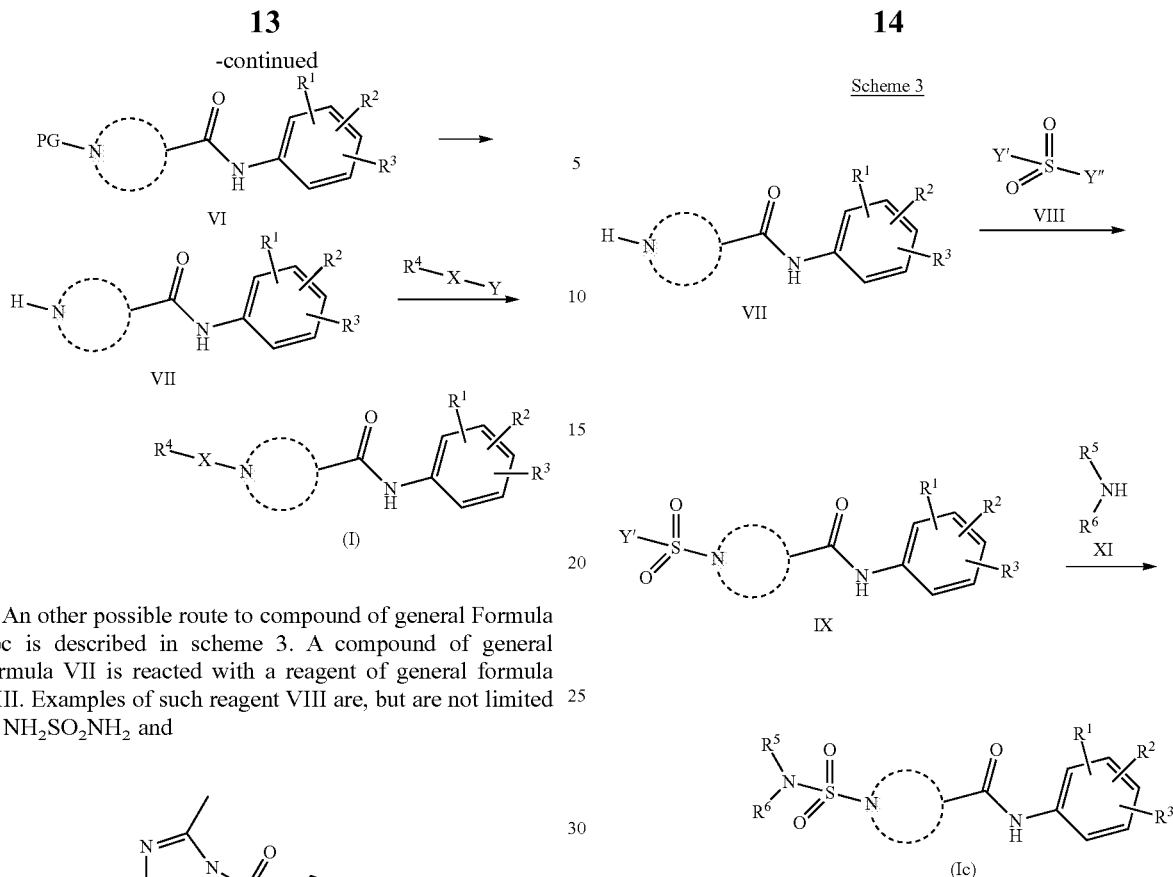

An other possible route to compound of general Formula (I)c is described in scheme 3. A compound of general formula VII is reacted with a reagent of general formula VIII. Examples of such reagent VIII are, but are not limited to $NH_2SO_2NH_2$ and

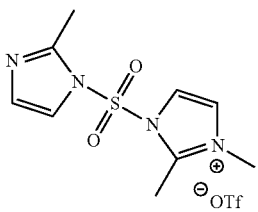

In case of

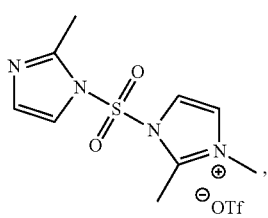 [SMILES: Cc1nccn1S(=O)(=O)n1cc[n+](C)c1C]

reaction with VII is followed by a methylation with for example MeOTf, resulting in a compound of general Formula (IXa):

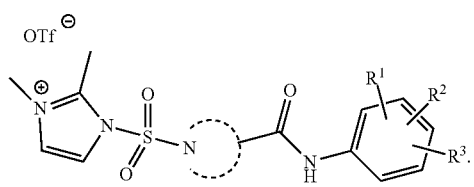

Further reaction with an amine of general formula XI, results in the formation of a compound of general Formula (Ic).

Scheme 3

General Procedure LCMS Methods

The High Performance Liquid Chromatography (HPLC) measurement was performed using a LC pump, a diode-array (DAD) or a UV detector and a column as specified in the respective methods. If necessary, additional detectors were included (see table of methods below). Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica., "Q-Tof" Quadrupole Time-of-flight mass spectrometers, "CLND", ChemiLuminescent Nitrogen Detector, "ELSD" Evaporative Light Scanning Detector, LCMS Methods (Flow expressed in mL/min; column temperature (T) in ° C.; Run time in minutes).

| Method LCMS | Instrument | Column | Mobile phase | Gradient | Flow Col T | Run time |
|---|---|---|---|---|---|---|
| A | Agilent 1100-UV 220 nm | YMC-PACK ODS-AQ, 50 × 2.0 mm 5 μm | A: 0.1% TFA in H₂O<br>B: 0.05 TFA in CH₃CN | 100% A held for 1 min from 100% A to 40% A in 4 min, held for 2.5 min, to 100% A in 0.5 min held for 2 min. | 0.8<br>50 | 10.0 |
| B | Agilent 1100-UV 220 nm | XBridge ShieldRP18, 50 * 2.1 mm 5 μm | A: 0.05% NH₃ in H₂O<br>B: CH₃CN | 100% A held for 1 min from 100% to 40% A in 4 min, held for 2.5 min, to 100% A in 0.5 min held for 2 min. | 0.8<br>40 | 10.0 |
| C | Waters: Acquity® UPLC®-DAD and SQD | Waters: BEH C18 (1.7 μm, 2.1 * 50 mm) | A: 10 mM CH₃COONH₄ in 95% H₂O + 5% CH₃CN<br>B: CH₃CN | From 95% A to 5% A in 1.3 min, held for 0.7 min. | 0.8<br>55 | 2 |
| D | Agilent 1100-UV 220 nm | YMC-PACK ODS-AQ, 50 × 2.0 mm 5 μm | A: 0.1% TFA in H₂O<br>B: 0.05 TFA in CH₃CN | 70% A held for 0.8 min from 70% to 10% A in 3.2 min, held for 2.5 min, to 70% A in 0.5 min held for 2 min. | 0.8<br>50 | 10.0 |
| E | Waters: Acquity® UPLC®-DAD and SQD | Waters: HSS T3 (1.8 μm, 2.1 * 100 mm) | A: 10 mM CH₃COONH₄ in 95% H₂O + 5% CH₃CN<br>B: CH₃CN | From 100% A to 5% A in 2.10 min, to 0% A in 0.90 min, to 5% A in 0.5 min | 0.8<br>55 | 3.5 |

SYNTHESIS OF COMPOUNDS

Compound 1: N-(4-fluoro-3-methyl-phenyl)-1-isobutylsulfonyl-pyrrolidine-3-carboxamide

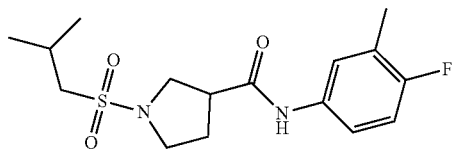 [SMILES: Cc1cc(NC(=O)C2CCN(S(=O)(=O)CC(C)C)C2)ccc1F]

To a stirred solution of 4-fluoro-3-methyl-aniline (2.0 g, 15.98 mmol), 1-tert-butoxycarbonylpyrrolidine-3-carboxylic acid (3.44 g, 15.98 mmol) and DIPEA (6.2 g, 47.9 mmol) in CH₂Cl₂ (30 mL), HATU (7.29 g, 19.2 mmol) was added at 0° C. The resulting mixture was stirred at 18° C. overnight. The reaction mixture was washed with 1N HCl (30 mL) and saturated aqueous NaHCO₃ (30 mL), dried over Na₂SO₄ and concentrated in vacuo, resulting in tert-butyl-3-[(4-fluoro-3-methyl-phenyl)carbamoyl]pyrrolidine-1-carboxylate (3.1 g). To a solution of tert-butyl 3-[(4-fluoro-3-methyl-phenyl)carbamoyl]pyrrolidine-1-carboxylate (3.1 g, 9.62 mmol) in CH₂Cl₂ (30 mL), trifluoroacetic (20 mL) acid was added. The resulting mixture was stirred at 18° C. for 3 hours. The reaction mixture was adjusted to pH=7-8 with saturated aqueous NaHCO₃. The organic layer was separated, washed with brine and dried over Na₂SO₄. The solvent was removed in vacuo and the obtained residue (1.8 g) was used as such in the next step. To part of the above obtained residue (500 mg) and DIPEA (576 mg, 4.46 mmol) in CH₂Cl₂ (10 mL), 2-methylpropane-1-sulfonyl chloride (257 mg, 1.64 mmol) was added at 0° C. The resulting mixture stirred at 18° C. for 4 hours. The reaction mixture was washed with 1N HCl (15 mL) and saturated aqueous NaHCO₃ (15 mL), dried over Na₂SO₄ and concentrated in vacuo. The crude product was purified by reversed phase preparative high-performance liquid chromatography (eluent: CH₃CN in H₂O (0.05% NH₃.H₂O) from 40% to 70%, v/v). The pure fractions were collected and the volatiles were removed in vacuo. The aqueous layer was lyophilized to dryness, resulting in compound 1 (40 mg).

Synthesis of Enantiomers of Compound 1

Compound 2: (3S)—N-(4-fluoro-3-methyl-phenyl)-1-isobutylsulfonyl-pyrrolidine-3-carboxamide

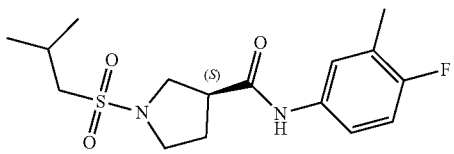

Prepared similarly as described for compound 1, starting from (3S)-1-tert-butoxycarbonylpyrrolidine-3-carboxylic acid instead of 1-tert-butoxycarbonylpyrrolidine-3-carboxylic acid. Method A; Rt: 5.43 min. m/z: 343.3 (M+H)⁺ Exact mass: 342.1. ¹H NMR (400 MHz, CHLOROFORM-d) δ ppm 1.13 (d, J=6.8 Hz, 6H) 2.22-2.37 (m, 6H) 2.83-3.00 (m, 2H) 3.10 (quin, J=7.3 Hz, 1H) 3.42-3.59 (m, 3H) 3.73 (dd, J=10.0, 7.5 Hz, 1H) 6.94 (t, J=8.9 Hz, 1H) 7.22-7.30 (m, 1H) 7.36-7.41 (m, 1H) 7.73 (br. s, 1H). [α]₃₆₅²⁰: +9.7° (c 0.26 w/v %, DMF).

Compound 3: (3R)—N-(4-fluoro-3-methyl-phenyl)-1-isobutylsulfonyl-pyrrolidine-3-carboxamide

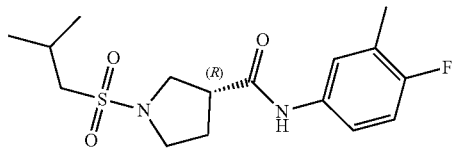

Prepared similarly as described for compound 1, starting from (3R)-1-tert-butoxycarbonylpyrrolidine-3-carboxylic acid instead of 1-tert-butoxycarbonylpyrrolidine-3-carboxylic acid. Method B; Rt: 5.54 min. m/z: 343.3 (M+H)+ Exact mass: 342.1. $[\alpha]_{365}^{20}$: −12.5° (c 0.46 w/v %, DMF)

Synthesis of (3S)—N-(4-fluoro-3-methyl-phenyl)pyrrolidine-3-carboxamide hydrochloride 4-fluoro-3-methylaniline (5.81 g, 46.5 mmol), Boc-(3S)-1-pyrrolidine-3-carboxylic acid (10 g, 46.5 mmol) and DIPEA (24 mL, 139.4 mmol) were dissolved in CH$_2$Cl$_2$ (30 mL). HATU (21.2 g, 55.7 mmol) was added in small portions and the resulted mixture was stirred overnight at room temperature. The reaction mixture was washed with 1M HCl (20 mL) and the organic layer was evaporated to dryness. The residue was purified by silica gel chromatography using a heptane to EtOAc gradient yielding tert-butyl (3S)-3-[(4-fluoro-3-methyl-phenyl)carbamoyl]pyrrolidine-1-carboxylate as a light brown oil (14.7 g). (3S)-3-[(4-fluoro-3-methyl-phenyl)carbamoyl]pyrrolidine-1-carboxylate (14.7 g) was dissolved in CH$_2$Cl$_2$ (100 mL) and HCl (6 M in iPrOH, 76 mL) was added. The reaction mixture was stirred overnight at room temperature. The volatiles were removed under reduced pressure and the obtained residue was triturated in diethylether, filtered and dried in vacuo overnight, yielding (3S)—N-(4-fluoro-3-methyl-phenyl)pyrrolidine-3-carboxamide hydrochloride as a powder (11.2 g).

General Synthetic Procedure A:

(3S)—N-(4-fluoro-3-methyl-phenyl)pyrrolidine-3-carboxamide hydrochloride (200 mg, 0.77 mmol) and DIPEA (2.5 eq) were dissolved in CH$_2$Cl$_2$ (5 mL). Reagent A (procedure A1: 0.140 mL; procedure A2: 0.150 mL if liquid or 1.1 eq when solid) was added and the reaction mixture was stirred overnight (procedure A1, A2 and A3), or 30 minutes (procedure A4) at room temperature.

Workup Procedure A1, A2 and A4: The mixture was washed with 1M HCl (5 mL) and the organic layer was loaded on a silica column and purified using gradient elution from heptane to EtOAc.

Workup Procedure A3: The organic layer was loaded on a silica column and purified using gradient elution from heptane to EtOAc.

| # | R$^4$–X– | Reagent A | Synthetic Procedure | LC-MS method | Rt (min.) | [M + NH$_4$]$^+$ or [M + H]$^+$ | Exact mass |
|---|---|---|---|---|---|---|---|
| 4 | methanesulfonyl group | Methanesulfonyl chloride | A1 | C | 0.80 | 318.1 | 300.1 |
| 5 | cyclopropanesulfonyl group | Cyclopropanesulfonyl chloride | A1 | C | 0.88 | 344.3 | 326.1 |
| 6 | 1-propanesulfonyl group | 1-Propanesulfonyl chloride | A1 | C | 0.93 | 346.2 | 328.1 |
| 7 | isopropylsulfonyl group | Isopropylsulfonyl chloride | A1 | C | 0.91 | 346.2 | 328.1 |

-continued

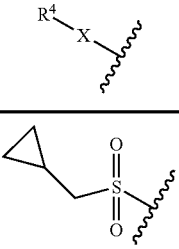

| # | R⁴\X | Reagent A | Synthetic Procedure | LC-MS method | Rt (min.) | [M + NH₄]⁺ or [M + H]⁺ | Exact mass |
|---|---|---|---|---|---|---|---|
| 8 | 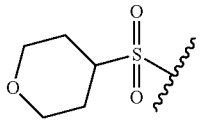 | Cyclopropylmethane-sulfonyl chloride | A1 | C | 0.93 | 358.2 | 340.1 |
| 9 | 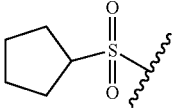 [SMILES: *S(=O)(=O)C1CCCC1] | Tetrahydro-2H-pyran-4-sulfonyl chloride | A1 | C | 0.85 | 388.2 | 370.1 |
| 10 | 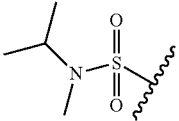 | Cyclopentanesulfonyl chloride | A1 | C | 0.99 | 372.1 | 354.1 |
| 11 | 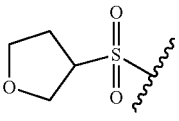 | N-Isopropyl-N-methyl-sulfamoyl chloride | A2 | C | 1.00 | 358.2 | 357.2 |
| 12 | 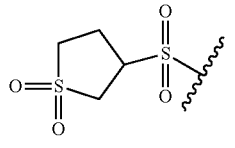 [SMILES: *S(=O)(=O)C1CCS(=O)(=O)C1] | Tetrahydro-3-furansulfonyl chloride | A2 | C | 0.83 | 374.3 | 356.1 |
| 13 | 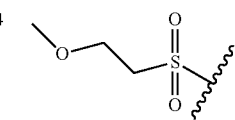 | 1,1-Dioxothiolane-3-sulfonyl chloride | A2 | C | 0.82 | 422.2 | 404.1 |
| 14 | 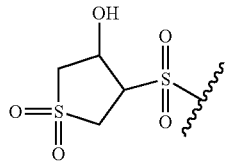 [SMILES: *S(=O)(=O)C1CS(=O)(=O)CC1O] | 2-Methoxy-ethanesulfonyl chloride | A2 | C | 0.85 | 362.1 | 344.1 |
| 15 | 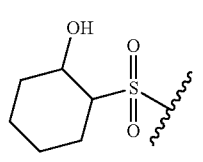 [SMILES: *S(=O)(=O)C1CCCCC1O] | 4-Hydroxy-1,1-dioxo-thiolane-3-sulfonyl chloride | A2 | C | 0.76/ 0.77 | 438.2 | 420.1 |
| 16 |  | 2-Hydroxycyclohexane-sulfonyl chloride | A2 | C | 0.90 | 402.2 | 384.2 |

-continued

| # | R⁴–X– structure | Reagent A | Synthetic Procedure | LC-MS method | Rt (min.) | [M + NH₄]⁺ or [M + H]⁺ | Exact mass |
|---|---|---|---|---|---|---|---|
| 17 | (isobutyl)(methyl)CH-SO₂– | 4-Methylpentane-2-sulfonyl chloride | A2 | C | 1.11 | 388.2 | 370.2 |
| 18 | MeO-CH₂-CH(Me)-SO₂– | 1-Methoxypropane-2-sulfonyl chloride | A2 | C | 0.90 | 376.2 | 358.1 |
| 19 | (Et)₂CH-SO₂– | Pentane-3-sulfonyl chloride | A2 | C | 1.05 | 374.2 | 356.2 |
| 20 | oxetan-3-yl-O-C(O)– | (2,5-dioxopyrrolidin-1-yl)oxetan-3-yl carbonate | A3 | C | 0.79 | 340.1 | 322.1 |
| 21 | iPrO-C(O)– | Isopropyl chloroformate | A3 | C | 0.96 | 326.2 | 308.2 |
| 22 | MeO-C(O)– | Methyl chloroformate | A3 | C | 0.82 | 298.2 | 280.1 |
| 23 | cyclohexyl-SO₂– | Cyclohexanesulfonyl chloride | A4 | C | 1.05 | 386.2 | 368.2 |
| 24 | (2-ethylcyclopropyl)-SO₂– | 2-Ethyl-cyclopropane-sulfonyl chloride | A4 | C | 1.00 | 372.1 | 354.1 |
| 25 | sec-butyl-SO₂– | Sec-butylsulfonyl chloride | A4 | C | 0.97 | 360.2 | 342.1 |

-continued

| # | Reagent A | R⁴−X− | Synthetic Procedure | LC-MS method | Rt (min.) | [M + NH₄]⁺ or [M + H]⁺ | Exact mass |
|---|---|---|---|---|---|---|---|
| 26 | Isobutyl chloroformate | | A4 | C | 1.03 | 340.2 | 322.2 |

Compound 6: (3S)—N-(4-fluoro-3-methyl-phenyl)-1-propylsulfonyl-pyrrolidine-3-carboxamide ¹H NMR (400 MHz, DMSO-d₆) δ ppm 1.00 (t, J=7.5 Hz, 3H), 1.66-1.77 (m, 2H), 2.01-2.12 (m, 1H), 2.12-2.19 (m, 1H), 2.20 (d, J=1.8 Hz, 3H), 3.04-3.11 (m, 2H), 3.17 (quin, J=7.4 Hz, 1H), 3.27-3.31 (m, 1H), 3.34-3.43 (m, 2H), 3.56 (dd, J=10.0, 7.8 Hz, 1H), 7.07 (t, J=9.2 Hz, 1H), 7.34-7.43 (m, 1H), 7.50 (dd, J=7.0, 2.4 Hz, 1H), 10.02 (s, 1H).

Compound 8: (3S)-1-(cyclopropylmethylsulfonyl)-N-(4-fluoro-3-methyl-phenyl)pyrrolidine-3-carboxamide ¹H NMR (400 MHz, DMSO-d₆) δ ppm 0.31-0.39 (m, 2H), 0.55-0.64 (m, 2H), 0.97-1.10 (m, 1H), 2.01-2.12 (m, 1H), 2.12-2.19 (m, 1H), 2.20 (d, J=1.8 Hz, 3H), 3.07 (d, J=7.0 Hz, 2H), 3.18 (quin, J=7.6 Hz, 1H), 3.33-3.38 (m, 1H), 3.38-3.47 (m, 2H), 3.59 (dd, J=9.7, 7.9 Hz, 1H), 7.07 (t, J=9.2 Hz, 1H), 7.35-7.43 (m, 1H), 7.50 (dd, J=7.0, 2.2 Hz, 1H), 10.02 (s, 1H).

Compound 9: (3S)—N-(4-fluoro-3-methyl-phenyl)-1-tetrahydropyran-4-ylsulfonyl-pyrrolidine-3-carboxamide ¹H NMR (400 MHz, DMSO-d₆) δ ppm 1.59-1.75 (m, 2H), 1.81-1.94 (m, 2H), 2.02-2.19 (m, 2H), 2.20 (d, J=1.8 Hz, 3H), 3.18 (quin, J=7.4 Hz, 1H), 3.32-3.56 (m, 6H), 3.62 (dd, J=9.7, 7.9 Hz, 1H), 3.87-3.98 (m, 2H), 7.07 (t, J=9.1 Hz, 1H), 7.34-7.43 (m, 1H), 7.50 (dd, J=7.0, 2.4 Hz, 1H), 10.02 (s, 1H).

Compound 10: (3S)-1-cyclopentylsulfonyl-N-(4-fluoro-3-methyl-phenyl)pyrrolidine-3-carboxamide ¹H NMR (400 MHz, DMSO-d₆) δ ppm 1.49-1.61 (m, 2H), 1.61-1.73 (m, 2H), 1.77-1.89 (m, 2H), 1.89-2.01 (m, 2H), 2.03-2.18 (m, 2H), 2.20 (d, J=1.8 Hz, 3H), 3.16 (quin, J=7.5 Hz, 1H), 3.33-3.46 (m, 3H), 3.60 (dd, J=9.7, 7.9 Hz, 1H), 3.71 (quin, J=8.1 Hz, 1H), 7.07 (t, J=9.2 Hz, 1H), 7.35-7.42 (m, 1H), 7.50 (dd, J=7.0, 2.4 Hz, 1H), 10.02 (s, 1H)

Compound 24: (3S)-1-(2-ethylcyclopropyl)sulfonyl-N-(4-fluoro-3-methyl-phenyl)pyrrolidine-3-carboxamide ¹H NMR (400 MHz, DMSO-d₆) δ ppm 0.81-0.90 (m, 1H), 0.92-0.98 (m, 3H), 1.05-1.13 (m, 1H), 1.28-1.42 (m, 3H), 2.01-2.19 (m, 2H), 2.19-2.23 (m, 3H), 2.52-2.54 (m, 1H), 3.13-3.24 (m, 1H), 3.33-3.38 (m, 1H), 3.38-3.48 (m, 2H), 3.54-3.63 (m, 1H), 7.07 (t, J=9.2 Hz, 1H), 7.36-7.43 (m, 1H), 7.48-7.54 (m, 1H), 10.02 (s, 1H).

The mixture 24 was separated in 2 isomers by Prep SFC (Stationary phase: Chiralcel Diacel OJ 20×250 mm), mobile phase: CO₂, iPrOH with 0.2% iPrNH₂). OJ-H 250 mm×4.6 mm, Flow: 5 mL/min, Mobile phase: 15% EtOH (containing 0.2% iPrNH₂) hold 4 min. Rt: 24a: 1.68 min, 24b: 2.04 min.

Compound 25: (3S)—N-(4-fluoro-3-methyl-phenyl)-1-sec-butylsulfonyl-pyrrolidine-3-carboxamide ¹H NMR (400 MHz, DMSO-d₆) δ ppm 0.96 (t, J=7.5 Hz, 3H) 1.22-1.26 (m, 3H) 1.36-1.54 (m, 1H) 1.81-1.97 (m, 1H) 2.02-2.18 (m, 2H) 2.20 (d, J=1.8 Hz, 3H) 3.09-3.26 (m, 2H) 3.33-3.48 (m, 3H) 3.57-3.66 (m, 1H) 7.06 (t, J=9.2 Hz, 1H) 7.33-7.43 (m, 1H) 7.51 (dd, J=7.0, 2.6 Hz, 1H) 10.02 (s, 1H)

Compound 26: isobutyl (3S)-3-[(4-fluoro-3-methyl-phenyl)carbamoyl]pyrrolidine-1-carboxylate ¹H NMR (400 MHz, DMSO-d₆) δ ppm 0.89 (d, J=6.6 Hz, 6H), 1.80-1.92 (m, 1H), 1.94-2.18 (m, 2H), 2.18-2.24 (m, 3H), 3.04-3.21 (m, 1H), 3.24-3.38 (m, 1H), 3.35-3.50 (m, 2H), 3.50-3.63 (m, 1H), 3.77 (d, J=6.4 Hz, 2H), 7.06 (t, J=9.2 Hz, 1H), 7.35-7.42 (m, 1H), 7.49-7.52 (m, 1H), 10.00 (s, 1H).

Compound 27: (1S,5S)—N-(4-fluoro-3-methyl-phenyl)-3-isobutylsulfonyl-3-azabicyclo[3.1.0]hexane-1-carboxamide

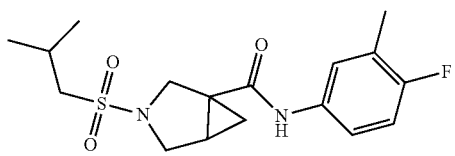 [SMILES: Cc1cc(NC(=O)C23CC2CN(S(=O)(=O)CC(C)C)C3)ccc1F]

Ethyl 3-benzyl-3-azabicyclo[3.1.0]hexane-5-carboxylate (1.03 g, 4.2 mmol) was dissolved in THF (40 mL). Water (10 mL) and LiOH (0.5 g, 20.9 mmol) were added. The reaction mixture was stirred at room temperature for 12 hours and next refluxed for 24 hours. The reaction mixture was concentrated to dryness in vacuo, and residual water was removed by coevaporation with toluene (2×20 mL), resulting in a residue. The obtained residue was suspended in $CH_2Cl_2$ (50 mL, dry) and $NEt_3 \cdot HCl$ (5.8 g, 42.0 mmol), 4-fluoro-3-methyl-aniline (0.79 g) and HATU (4.8 g, 12.6 mmol) were added successively. The reaction mixture was stirred at room temperature for 2 hours. DMF (100 mL) and more 4-fluoro-3-methyl-aniline (0.53 g) was added to the reaction mixture. The reaction mixture was further stirred at room temperature over weekend. The reaction mixture was diluted with $CH_2Cl_2$ (100 mL), washed with saturated aqueous sodium bicarbonate (2×50 mL), dried ($Na_2SO_4$), and concentrated in vacuo resulting in a residue. The obtained residue was purified using silica gel column chromatography by gradient elution with ethyl acetate in heptane from 0 to 100% and next ethylacetate in heptane from 20 to 25% resulting in 3-benzyl-N-(4-fluoro-3-methyl-phenyl)-3-azabicyclo[3.1.0]hexane-5-carboxamide (400 mg). Method C; Rt: 1.17 min. m/z: 325.2 (M+H)$^+$ Exact mass: 324.2. 3-benzyl-N-(4-fluoro-3-methyl-phenyl)-3-azabicyclo[3.1.0] hexane-5-carboxamide (400 mg) was dissolved in methanol (50 mL) and Pd/C 10% (262 mg) was added. The solution was stirred under H2 atmosphere for 1 hour at room temperature. After filtration on dicalite, the mixture was concentrated in vacuo, resulting in N-(4-fluoro-3-methyl-phenyl)-3-azabicyclo[3.1.0]hexane-5-carboxamide (282 mg). Method C; Rt: 0.60 min. m/z: 235.2 (M+H)$^+$ Exact mass: 234.1. To a solution of N-(4-fluoro-3-methyl-phenyl)-3-azabicyclo[3.1.0]hexane-5-carboxamide (142 mg, 0.606 mmol) in $CH_2Cl_2$ (5 mL) was added DIPEA (0.84 mL, 4.85 mmol) and 2-methylpropane-1-sulfonyl chloride (142.4 mg, 0.91 mmol). The reaction mixture was stirred at room temperature for 30 minutes and then diluted with $CH_2Cl_2$ (10 mL), washed with aqueous HCl (1 N, 10 mL), brine and dried ($Na_2SO_4$). After removal of the volatiles in vacuo, the obtained residue was purified using silica gel column chromatography (ethyl acetate in heptane from 20-30%) resulting in a sticky residue. This residue was triturated in diisopropylether and the obtained white solid was filtered, washed with petroleum ether and dried in vacuo, resulting in compound 27 (124 mg) as a white powder. Method C; Rt: 1.02 min. m/z: 372.2 (M+NH$_4$)$^+$ Exact mass: 354.1. $^1$H NMR (400 MHz, CHLOROFORM-d) δ ppm 1.11 (d, J=6.8 Hz, 6H), 1.17 (t, J=5.2 Hz, 1H), 1.52 (dd, J=8.4, 5.3 Hz, 1H), 2.17 (ddd, J=8.4, 5.0, 3.9 Hz, 1H), 2.21-2.33 (m, 4H), 2.87 (d, J=6.6 Hz, 2H), 3.48 (dd, J=9.7, 3.7 Hz, 1H), 3.62 (d, J=9.5 Hz, 1H), 3.74 (d, J=9.0 Hz, 1H), 3.82 (d, J=8.8 Hz, 1H), 6.95 (t, J=8.9 Hz, 1H), 7.03 (br. s, 1H), 7.17-7.24 (m, 1H), 7.34 (dd, J=6.6, 2.6 Hz, 1H).

Compound 28: N-(4-fluoro-3-methyl-phenyl)-1-isobutylsulfonyl-indoline-3-carboxamide

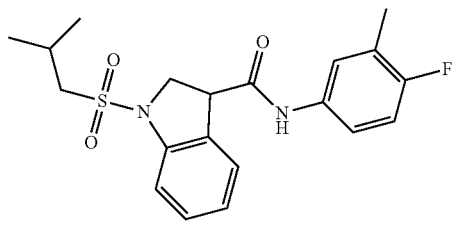 [SMILES: Cc1cc(NC(=O)C2CN(S(=O)(=O)CC(C)C)c3ccccc32)ccc1F]

Indoline-3-carboxylic acid (1 g, 6.13 mmol) was dissolved in DMF (10 mL) and water (5 mL) was added. After addition of DIPEA (2.4 mL, 14.1 mmol), the reaction mixture was stirred for 10 minutes. Then, 2-methylpropane-1-sulfonyl chloride (0.96 g, 6.128 mmol) was added dropwise and the reaction mixture was stirred overnight at room temperature. The reaction mixture was partitioned between $CH_2Cl_2$ and water set to pH=10 with 1M NaOH. The organic layer was removed and the aqueous layer was acidified with conc. HCl to pH=1. The product was extracted with $CH_2Cl_2$. The organic layer was dried with $MgSO_4$, filtered and concentrated to dryness in vacuo, yielding 1-isobutylsulfonylindoline-3-carboxylic acid as an oil (600 mg), which was used as such in the next step. 1-isobutylsulfonylindoline-3-carboxylic acid (600 mg), 4-fluoro-3-methylaniline (265 mg, 2.12 mmol) and DIPEA (1.1 mL, 6.35 mmol) were dissolved in $CH_2Cl_2$ (20 mL). HATU (966.2 mg, 2.54 mmol) was added and the resulting mixture was stirred overnight at room temperature. The reaction mixture was washed with 1M HCl (15 mL) and the organic layer was evaporated to dryness. The obtained residue was purified by silica gel column chromatography using a heptane to EtOAc gradient yielding compound 28 (36.2 mg) as an off-white powder. Method E; Rt: 2.03 min. m/z: 391.0 (M+H)$^+$ Exact mass: 390.1. $^1$H NMR (400 MHz, DMSO-d$_6$) ppm 1.04 (d, J=6.8 Hz, 3H), 1.03 (d, J=6.6 Hz, 3H), 2.11-2.19 (m, 1H), 2.21 (d, J=1.3 Hz, 3H), 3.00-3.17 (m, 2H), 4.14-4.22 (m, 1H), 4.23-4.31 (m, 1H), 4.31-4.38 (m, 1H), 7.01-7.13 (m, 2H), 7.23-7.34 (m, 2H), 7.38-7.48 (m, 2H), 7.52 (dd, J=7.0, 2.4 Hz, 1H), 10.42 (s, 1H)

Compound 29: N-(4-fluoro-3-methyl-phenyl)-1-isobutylsulfonyl-3-methyl-pyrrolidine-3-carboxamide

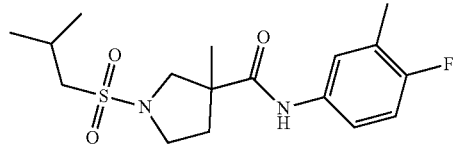 [SMILES: Cc1cc(NC(=O)C2(C)CCN(S(=O)(=O)CC(C)C)C2)ccc1F]

Synthesised similarly as described for compound 28, using 3-methyl-pyrrolidine-3-carboxylic acid instead of indoline-3-carboxylic acid. Method C; Rt: 1.04 min. m/z: 374.3 (M+NH$_4$)$^+$ Exact mass: 356.2. $^1$H NMR (400 MHz, DMSO-d$_6$) ppm 0.97-1.03 (m, 6H), 1.39 (s, 3H), 1.81-1.92 (m, 1H), 2.03-2.15 (m, 1H), 2.21 (d, J=1.8 Hz, 3H), 2.38-2.47 (m, 1H), 2.93 (d, J=6.6 Hz, 2H), 3.20 (d, J=9.9 Hz, 1H), 3.23-3.30 (m, 1H), 3.33-3.41 (m, 1H), 3.75 (d, J=9.9 Hz, 1H), 7.07 (t, J=9.1 Hz, 1H), 7.38-7.47 (m, 1H), 7.52 (dd, J=7.0, 2.4 Hz, 1H), 9.56 (s, 1H). The racemic mixture 29 was separated in enantiomers 29a and 29b by preparative SFC (Stationary phase: Chiralpak Diacel AS 20×250 mm), Mobile phase: CO$_2$, MeOH with 0.4% iPrNH$_2$). AS-H 250 mm×4.6 mm, Flow: 5 mL/min, Mobile phase: 20% MeOH (containing 0.2% iPrNH$_2$) hold 7 min. Rt: 29a: 1.36 min, 29b: 1.72 min.

Compound 30: N-(4-fluoro-3-methyl-phenyl)-7-isobutylsulfonyl-7-azabicyclo[2.2.1]heptane-3-carboxamide (Racemic Mixture, Diastereomeric Pure)

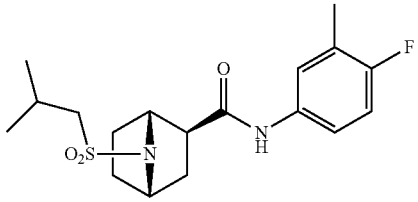 [SMILES: Cc1cc(NC(=O)[C@H]2C[C@@H]3CC[C@H]2N3S(=O)(=O)CC(C)C)ccc1F]

4-fluoro-3-methylaniline (0.622 g, 4.97 mmol) was dissolved in CH$_2$Cl$_2$ (60 mL). Then (+/−)-7-tert-butoxycarbonyl-7-azabicyclo[2.2.1]heptane-3-carboxylic acid (1 g, 4.14 mmol) was added followed by DIPEA (2.14 mL, 12.4 mmol) and this mixture was stirred for 10 minutes. Then, HATU (2.36 g, 6.12 mmol) was added portion wise. The resulting mixture was stirred for 1.5 hours. Then, NaOH (1M in H$_2$O, 16.6 mL) was added. The resulting mixture was extracted with CH$_2$Cl$_2$ (3×25 mL) and the combined organics were dried (MgSO$_4$), filtered and concentrated in vacuo. The obtained crude was purified using silica gel column chromatography (gradient elution: EtOAc-heptane 0:100 to 30:70), resulting in tert-butyl 3-[(4-fluoro-3-methyl-phenyl)-carbamoyl]-7-azabicyclo[2.2.1]heptane-7-carboxylate (77 mg). Tert-butyl 3-[(4-fluoro-3-methyl-phenyl)carbamoyl]-7-azabicyclo[2.2.1]heptane-7-carboxylate (77 mg) was dissolved in 1,4-dioxane (2 mL) and HCl (4 M in dioxane, 0.88 mL) was added in 3 portions over 1 hour. 30 minutes after the last addition, the mixture was concentrated at 50° C. under a gentle flow of nitrogen. The obtained crude was used as such. Method C; Rt: 0.58 min. m/z: 249.2 (M+H)$^+$ Exact mass: 248.1. The above obtained crude was stirred in CH$_2$Cl$_2$ (2 mL) and DIPEA (0.30 mL, 1.8 mmol) was added, followed by 2-methylpropane-1-sulfonyl chloride (43 μL, 0.331 mL). The reaction mixture was stirred overnight. The reaction mixture was poured into dichloromethane (5 mL) and treated with HCl (1M in H$_2$O, 2.2 mL). The layers were separated and the organics were dried on MgSO$_4$, filtered and concentrated in vacuo. The obtained crude was chromatographed using silica gel column chromatography (gradient elution: EtOAc-heptane 0:100 to 20:80). The combined fractions were concentrated and the obtained residue was dried in vacuo, resulting in compound 30 (32.1 mg). Method C; Rt: 1.04 min. m/z: 386.3 (M+NH$_4$)+ Exact mass: 368.2. $^1$H NMR (400 MHz, CHLOROFORM-d) δ ppm 1.10 (d, J=6.5 Hz, 6H), 1.56-1.64 (m, 2H), 1.92 (dd, J=12.3, 9.5 Hz, 1H), 2.01-2.14 (m, 2H), 2.14-2.20 (m, 1H), 2.25 (d, J=2.0 Hz, 3H), 2.33 (spt, J=6.7 Hz, 1H), 2.60 (dd, J=9.1, 5.0 Hz, 1H), 2.92-3.05 (m, 2H), 4.31 (t, J=4.4 Hz, 1H), 4.47 (d, J=4.4 Hz, 1H), 6.93 (t, J=8.9 Hz, 1H), 7.21-7.30 (m, 1H), 7.35 (dd, J=6.9, 2.4 Hz, 1H), 7.76 (br. s., 1H).

Compound 31: (3S)—N-(4-fluoro-3-methyl-phenyl)-1-(isobutylsulfamoyl)pyrrolidine-3-carboxamide

(3S)—N-(4-fluoro-3-methyl-phenyl)pyrrolidine-3-carboxamide hydrochloride (50 mg, 0.193 mmol) and NH$_2$SO$_2$NH$_2$ (93 mg, 0.966 mmol) were suspended in dioxane (3 mL) in a sealed microwave tube. The tube was heated overnight at 100° C. The reaction mixture was used as such in the next reaction. To the above reaction mixture, isobutylamine was added (1 mL). The tube was heated overnight at 100° C. The reaction mixture was evaporated to dryness and purified on silica using a heptane to EtOAc gradient, followed by preparative HPLC (RP Vydac Denali C18—10 μm, 250 g, 5 cm). Mobile phase (0.25% NH$_4$HCO$_3$ solution in water, MeOH), the desired fractions were collected, evaporated, dissolved in MeOH and evaporated again, resulting in compound 31 (3.5 mg). Method C; Rt: 0.98 min. m/z: 375.2 (M+NH$_4$)$^+$ Exact mass: 357.2. $^1$H NMR (400 MHz, DMSO-d$_6$) δ ppm 0.86 (d, J=6.8 Hz, 6H), 1.62-1.74 (m, 1H), 1.99-2.18 (m, 2H), 2.20 (d, J=1.8 Hz, 3H), 2.73 (d, J=6.8 Hz, 2H), 3.09-3.30 (m, 4H), 3.47 (dd, J=9.5, 8.1 Hz, 1H), 7.06 (t, J=9.1 Hz, 1H), 7.17 (br. s., 1H), 7.35-7.44 (m, 1H), 7.51 (dd, J=7.2, 2.3 Hz, 1H), 10.02 (br. s., 1H).

Compound 32: (3S)—N-(4-fluoro-3-methyl-phenyl)-1-(isopropylsulfamoyl)pyrrolidine-3-carboxamide

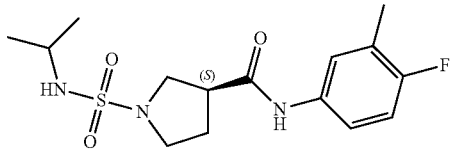

Catechol (10 g, 90.8 mmol) and pyridine (14.6 mL, 181.6 mmol) dissolved in heptane (60 mL) were stirred at −5° C. Sulfuryl chloride (12.26 g, 90.8 mmol) dissolved in heptanes (20 mL) was added dropwise while maintaining the temperature at −5° C. After complete addition, the reaction mixture was stirred for 2 hours at −5° C. The reaction mixture was allowed to reach room temperature and was used as such in the next step. Isopropylamine (7.7 mL, 90.8 mmol) and then NEt$_3$ (12.6 mL, 90.8 mmol) where added to the above obtained reaction mixture at room temperature. The reaction mixture was stirred for 3 hours at room temperature. The reaction mixture was poured in a CH$_2$Cl$_2$/water mixture. The organic layer was separated and evaporated to dryness. The obtained residue was purified by silica gel column chromatography applying gradient elution from heptane to EtOAc. The product fractions were collected and evaporated to dryness yielding (2-hydroxyphenyl) N-isopropylsulfamate (3.28 g). $^1$H NMR (400 MHz, DMSO-d$_6$) δ ppm 1.14 (d, J=6.6 Hz, 6H), 3.56-3.68 (m, 1H), 6.77-6.83 (m, 1H), 6.95 (dd, J=8.0, 1.7 Hz, 1H), 7.05-7.12 (m, 1H), 7.25 (dd, J=8.1, 1.8 Hz, 1H), 8.05 (d, J=7.0 Hz, 1H), 9.75 (s, 1H). (3S)—N-(4-fluoro-3-methyl-phenyl)pyrrolidine-3-carboxamide hydrochloride, (2-hydroxyphenyl) N-isopropylsulfamate (300 mg, 1.30 mmol) and NEt$_3$ (0.134 mL, 0.966 mmol) were dissolved in CH$_3$CN (3 mL) and heated in the microwave for 10 minutes at 100° C. The tube was heated again for 15 minutes at 100° C. More NEt$_3$ (0.1 mL) was added and the tube was heated again for 30 minutes. The volatiles were removed under reduced pressure and the residue was purified by silica gel column chromatography using a heptane to EtOAc gradient, followed by prep. HPLC. (RP Vydac Denali C18-10 μm, 250 g, 5 cm). Mobile phase (0.25% NH₄HCO₃ solution in water, MeOH), the desired fractions were collected, evaporated, dissolved in MeOH and evaporated again, the obtained residue was crystallized from CH₃CN/diisopropylether, resulting in compound 32 (95.8 mg). Method C; Rt: 0.91 min. m/z: 344.2 (M+H)⁺ Exact mass: 343.1. ¹H NMR (400 MHz, DMSO-d₆) δ ppm 1.09-1.13 (m, 6H), 1.98-2.18 (m, 2H), 2.20 (d, J=1.8 Hz, 3H), 3.09-3.29 (m, 4H), 3.34-3.50 (m, 2H), 7.02-7.11 (m, 2H), 7.34-7.42 (m, 1H), 7.50 (dd, J=7.0, 2.4 Hz, 1H), 10.00 (s, 1H); Differential scanning calorimetry (From 30 to 300° C. at 10° C./min), Peak: 101.1° C. [α]$_D^{20}$: −6.2° (c 0.54 w/v %, DMF)

Compound 33: (3S)—N-(4-fluoro-3-methyl-phenyl)-1-[[(3S)-tetrahydrofuran-3-yl]sulfamoyl]pyrrolidine-3-carboxamide

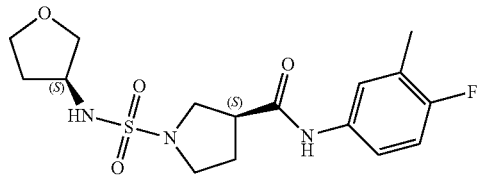

(S)-(−)-3-aminotetrahydrofuran p-toluenesulfonate (301.3 mg, 1.16 mmol) was added to a stirred mixture of 1,3,2-Benzodioxathiole 2,2-dioxide (200 mg, 1.16 mmol) and NEt₃ (484 μL, 3.49 mmol) in 1,4-dioxane (10 mL). (3S)—N-(4-fluoro-3-methyl-phenyl)pyrrolidine-3-carboxamide hydrochloride (258 mg) was added to the reaction mixture. The mixture was heated at 100° C. for 10 minutes, cooled to room temperature, heated at 100° C. for 30 minutes more and cooled to room temperature. The reaction mixture was stored at room temperature over weekend. The mixture was filtered, the filtrate was concentrated and the obtained residue was diluted with CH₂Cl₂ (10 mL). The organic layer was washed with aqueous hydrochloric acid (1N, 2×10 mL), dried (Na₂SO₄) and evaporated to dryness. The residue was purified using silica gel column chromatography by gradient elution with ethyl acetate in heptanes, resulting in compound 33 (51 mg). Method C; Rt: 0.80 min. m/z: 372.2 (M+H)⁺ Exact mass: 371.1. ¹H NMR (400 MHz, DMSO-d₆) δ ppm 1.75-1.88 (m, 1H), 1.98-2.18 (m, 3H), 2.20 (d, J=1.8 Hz, 3H), 3.10-3.35 (m, 4H), 3.41-3.54 (m, 2H), 3.65 (td, J=8.0, 5.9 Hz, 1H), 3.70-3.81 (m, 2H), 3.82-3.92 (m, 1H), 7.06 (t, J=9.1 Hz, 1H), 7.35-7.43 (m, 1H), 7.46 (br. s, 1H), 7.51 (dd, J=7.0, 2.2 Hz, 1H), 10.02 (br. s, 1H). [α]$_D^{20}$: −6.4° (c 0.63 w/v %, DMF).

Compound 34: (3S)—N-(4-fluoro-3-methyl-phenyl)-1-[(3-methyloxetan-3-yl)sulfamoyl]pyrrolidine-3-carboxamide

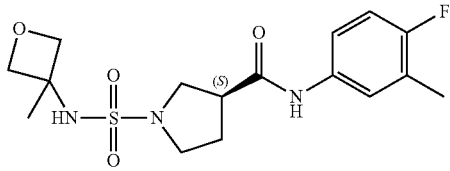

2,3-Dimethyl-1-[(2-methyl-1H-imidazol-1-yl)sulfonyl]-1H-imidazol-3-ium trifluoromethanesulfonate (1.51 g, 3.87 mmol), (3S)—N-(4-fluoro-3-methyl-phenyl)pyrrolidine-3-carboxamide hydrochloride (500 mg, 1.93 mmol) and DIPEA (1.67 mL, 9.66 mmol) were dissolved in CH₃CN (5 mL) and stirred for 30 minutes at room temperature. The volatiles were removed under reduced pressure and the obtained residue was purified by silica gel column chromatography from heptane to EtOAc gradient resulting in (3S)—N-(4-fluoro-3-methyl-phenyl)-1-(2-methylimidazol-1-yl)sulfonyl-pyrrolidine-3-carboxamide (387 mg). (3S)—N-(4-fluoro-3-methyl-phenyl)-1-(2-methylimidazol-1-yl)sulfonyl-pyrrolidine-3-carboxamide (387 mg, 1.056 mmol) was dissolved in CH₂Cl₂ (10 mL) and the mixture was cooled with an ice bath. Methyl trifluoromethanesulfonate (190.7 mg, 1.16 mmol) was added and the reaction mixture was stirred for 2 hours at 0° C. The volatiles were removed under reduced pressure and the obtained residue was dissolved in CH₃CN (10 mL), together with 3-methyl-3-oxetanamine hydrochloride (1:1) (163.1 mg, 1.32 mmol) and DIPEA (0.364 mL, 2.11 mmol). The mixture was heated 1 hour at 80° C. The volatiles were removed under reduced pressure and the obtained residue was purified by silica gel column chromatography from heptanes to EtOAc gradient resulting in compound 34 (244 mg). ¹H NMR (400 MHz, DMSO-d₆) δ ppm 1.60 (s, 3H), 2.00-2.19 (m, 2H), 2.20 (d, J=1.8 Hz, 3H), 3.11-3.30 (m, 4H), 3.49 (dd, J=9.6, 8.3 Hz, 1H), 4.21 (d, J=6.3 Hz, 2H), 4.65 (d, J=6.3 Hz, 2H), 7.06 (t, J=9.2 Hz, 1H), 7.34-7.43 (m, 1H), 7.51 (dd, J=7.0, 2.4 Hz, 1H), 7.62 (s, 1H), 10.02 (s, 1H). Method C; Rt: 0.81 min. m/z: 389.2 (M+NH₄)⁺ Exact mass: 371.1.

Compound 35: 3-fluoro-N-(4-fluoro-3-methyl-phenyl)-1-(isopropylsulfamoyl)pyrrolidine-3-carboxamide

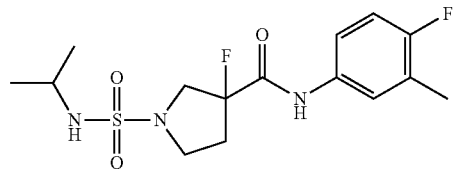 [SMILES: Cc1cc(NC(=O)C2(F)CCN(S(=O)(=O)NC(C)C)C2)ccc1F]

To a solution of 1-benzyl-3-fluoro-pyrrolidine-3-carboxylic acid (3.06 g, 13.7 mmol) (synthesis described in Tetrahedron Letters (2011), 52(12), 1300-1302) in DMF (30 mL) was added triethylamine hydrochloride (9.43 g, 68.5 mmol), triethylamine (5.71 mL, 41.1 mmol), HATU (4.83 g, 20.6 mmol) and 4-fluoro-3-methyl-aniline (1.71 g, 13.7 mmol). The reaction mixture was stirred at room temperature for 1 hour and diluted with water (200 mL). The solids were filtered and washed with water to afford 1-benzyl-3-fluoro-N-(4-fluoro-3-methyl-phenyl)pyrrolidine-3-carboxamide as a light purple powder (2.65 g). A second crop (120 mg) was isolated from the filtrate. Both powders were combined for the next step. 1-benzyl-3-fluoro-N-(4-fluoro-3-methyl-phenyl)pyrrolidine-3-carboxamide (2.77 g, 8.37 mmol) was dissolved in MeOH (150 mL) and 10% Pd on charcoal (0.89 g) was added. This mixture was hydrogenated at room temperature at a H2 pressure of 1 atm for 30 minutes. The solids were filtered off and the filtrate was evaporated under reduced pressure to afford 3-fluoro-N-(4-fluoro-3-methylphenyl)pyrrolidine-3-carboxamide (1.21 g) as an off white solid. Method E; Rt: 1.23 min. m/z: 241.4 (M+H)+ Exact mass: 240.1.

3-fluoro-N-(4-fluoro-3-methyl-phenyl)pyrrolidine-3-carboxamide (250 mg, 0.98 mmol), (2-hydroxyphenyl) N-isopropylsulfamate (294 mg, 1.27 mmol) and triethylamine (0.27 mL, 1.96 mmol) were dissolved in ACN (3 mL) and heated in the microwave for 10 minutes at 100° C. The volatiles were removed under reduced pressure. The residue was dissolved in DCM (20 mL) and washed with aqueous HCl (1 N) (2×5 mL) and brine (5 mL). The organic layer was concentrated to dryness and the residue was purified by silica gel chromatography by gradient elution with ethyl acetate in heptanes yielding a sticky oil. This was dissolved in methanol (2 mL). To this solution was added water (8 mL). The suspension was heated at reflux and the emulsion became suspension overnight. The solids were filtered and washed with methanol in water (20%, 2×2 mL) to afford compound 35 as a white solid which was dried in vacuum oven over weekend at 50° C. (210 mg). $^1$H NMR (400 MHz, DMSO-$d_6$) δ ppm 1.13 (dd, J=6.5, 0.8 Hz, 6H), 2.21 (d, J=1.8 Hz, 3H), 2.27-2.41 (m, 1H), 2.41-2.61 (m, 1H), 3.34-3.52 (m, 3H), 3.53-3.73 (m, 2H), 7.10 (t, J=9.2 Hz, 1H), 7.26 (br. d, J=7.3 Hz, 1H), 7.50 (ddd, J=8.7, 4.7, 2.9 Hz, 1H), 7.63 (dd, J=7.0, 2.2 Hz, 1H), 10.21 (br. s., 1H). Method C; Rt: 0.96 min. m/z: 379.2 (M+NH$_4$)+ Exact mass: 361.1.

The racemic mixture 35 was separated in enantiomers by Prep SFC (Stationary phase: Chiralcel Diacel OD 20×250 mm), mobile phase: CO$_2$, iPrOH with 0.4% iPrNH$_2$). OD-H 250 mm×4.6 mm, Flow: 5 mL/min, Mobile phase: 35% MeOH (containing 0.2% iPrNH$_2$) hold 4 min. Rt: 35a: 2.39 min, 35b: 2.87 min.

Compound 36: N-(4-fluoro-3-methyl-phenyl)-2-(isopropylsulfamoyl)-2-azabicyclo[3.1.0]hexane-4-carboxamide

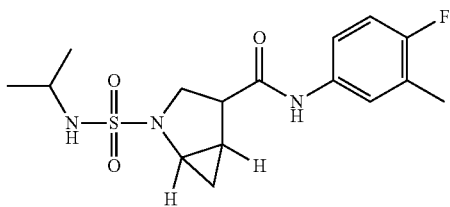 [SMILES: Cc1cc(NC(=O)C2CN(S(=O)(=O)NC(C)C)C3CC23)ccc1F]

To a solution of 2-tert-butoxycarbonyl-2-azabicyclo [3.1.0]hexane-4-carboxylic acid (1000 mg, 4.4 mmol) in DMF (10 mL) was added triethylamine (1.83 mL, 13.2 mmol), HATU (2.51 g, 6.60 mmol) followed by 4-fluoro-3-methyl-aniline (716 mg, 5.72 mmol). The reaction mixture was stirred at room temperature for 1 hour and diluted with water (100 mL). The solids were filtered and washed with water to afford tert-butyl 4-[(4-fluoro-3-methyl-phenyl)carbamoyl]-2-azabicyclo[3.1.0]hexane-2-carboxylate as a brown sticky solid. This was redissolved in DCM, dried over MgSO$_4$, filtered and used as such in the next step. Method C; Rt: 1.02 min and 1.05 min. m/z: 335.2 (M+H)+ Exact mass: 334.2.

To a solution of tert-butyl 4-[(4-fluoro-3-methyl-phenyl) carbamoyl]-2-azabicyclo[3.1.0]hexane-2-carboxylate (1.47 g, 4.4 mmol) in DCM (200 mL) was added TFA (6.73 mL, 88 mmol). The reaction mixture was stirred at room temperature for 5 hours. The reaction mixture was evaporated to dryness to afford N-(4-fluoro-3-methyl-phenyl)-2-azabicyclo[3.1.0]hexane-4-carboxamide as a brown oil. Method C; Rt: 0.58 min and 0.60 min. m/z: 235.2 (M+H)+ Exact mass: 234.1.

N-(4-fluoro-3-methyl-phenyl)-2-azabicyclo[3.1.0] hexane-4-carboxamide (300 mg, 0.86 mmol), (2-hydroxyphenyl) N-isopropylsulfamate (259 mg, 1.12 mmol) and triethylamine (0.36 mL, 2.58 mmol) were dissolved in ACN (5 mL) and heated in the microwave for 10 minutes at 100° C.

The volatiles were removed under reduced pressure and the residue was dissolved in DCM (20 mL), washed with aqueous HCl (1 M) (2×5 mL) and brine (5 mL). The organic layer was concentrated to dryness and the residue was purified using silica gel chromatography using a ethyl acetate in heptane gradient (from 20 to 100%) yielding compound 36a (TRANS-isomer) as a white powder (36 mg) $^1$H NMR (600 MHz, DMSO-$d_6$) δ ppm 0.62 (dt, J=8.7, 5.9 Hz, 1H), 0.94 (ddd, J=6.0, 4.7, 2.6 Hz, 1H), 1.12 (dd, J=6.6, 1.6 Hz, 6H), 1.78 (ddd, J=8.8, 6.0, 6 4.8 Hz, 1H), 2.20 (d, J=1.8 Hz, 3H), 2.95 (dd, J=10.5, 7.8 Hz, 1H), 3.12 (td, J=5.9, 2.7 Hz, 1H), 3.22 (dd, J=7.8, 1.1 Hz, 1H), 3.43 (q, J=6.5 Hz, 1H), 3.47 (d, J=10.4 Hz, 1H), 7.07 (t, J=9.2 Hz, 1H), 7.15 (br. s., 1H), 7.38-7.41 (m, 1H), 7.51 (dd, J=7.0, 2.2 Hz, 1H), 9.99 (s, 1H). Method C; Rt: 0.90 min. m/z: 356.1 (M+H)+ Exact mass: 355.1. and impure compound 36b as a colorless oil. This was further purified using prep. LCMS. (Hypersyl C18 BDS-3 μm, 100×4.6 mm) Mobile phase (NH$_4$HCO$_3$ 0.2% in water, acetonitrile). The desired fractions were combined and evaporated to dryness, dissolved in methanol again and evaporated to dryness and dried in a vacuum oven overnight to yield compound 36b (CIS-isomer) (40 mg). $^1$H NMR (600 MHz, DMSO-$d_6$) δ ppm 0.50 (dt, J=8.4, 6.1 Hz, 1H), 1.11 (ddd, J=6.3, 4.4, 2.9 Hz, 1H), 1.14 (dd, J=6.6, 2.9 Hz, 6H), 1.85-1.96 (m, 1H), 6 2.21 (d, J=1.8 Hz, 3H), 3.06-3.13 (m, 1H), 3.16 (td, J=6.1, 2.7 Hz, 1H), 3.28-3.31 (m, 1H), 3.33-3.35 (m, 1H), 3.39 (s, 1H), 3.41-3.50 (m, 1H), 7.07 (t, J=9.2 Hz, 1H), 7.21 (br. s., 1H), 7.39 (ddd, J=8.5, 4.6, 2.8 Hz, 1H), 7.53 (dd, J=7.1, 2.3 Hz, 1H), 10.07 (s, 1H). Method C; Rt: 0.92 min. m/z: 356.1 (M+H)+ Exact mass: 355.1

Compound 37: (3S)—N-(4-fluoro-3-methyl-phenyl)-1-[[(1R,2R)-2-hydroxyindan-1-yl]sulfamoyl] pyrrolidine-3-carboxamide

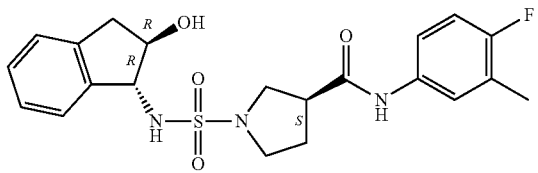

Compound 37 was prepared similarly as compound 34, using (1R,2R)-1-amino-2,3-dihydro-1H-inden-2-ol instead of 3-methyl-3-oxetanamine hydrochloride (1:1). $^1$H NMR (400 MHz, DMSO-$d_6$) δ ppm 2.05-2.18 (m, 2H), 2.20 (s, 3H), 2.67 (dd, J=15.5, 6.9 Hz, 1H), 3.06-3.25 (m, 2H), 3.33-3.43 (m, 3H), 3.61 (t, J=8.8 Hz, 1H), 4.22 (quin, J=6.4 Hz, 1H), 4.49 (t, J=7.0 Hz, 1H), 5.30 (d, J=5.7 Hz, 1H), 7.07 (t, J=9.2 Hz, 1H), 7.14-7.29 (m, 3H), 7.32-7.45 (m, 2H), 7.52 (dd, J=6.9, 2.3 Hz, 1H), 7.63 (d, J=8.1 Hz, 1H), 10.01 (s, 1H). Method C; Rt: 0.91 min. m/z: 434.2 (M+H)+ Exact mass: 433.1.

Compound 38: tert-butyl N-[2-[[(3S)-3-[(4-fluoro-3-methyl-phenyl)carbamoyl]pyrrolidin-1-yl]sulfonylamino]propyl]carbamate

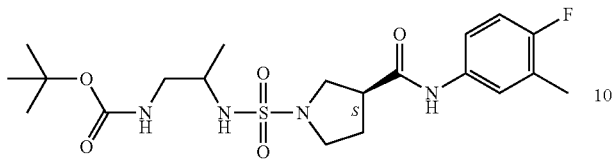

Compound 38 was prepared similarly as compound 34, using carbamic acid, N-(2-aminopropyl)-, 1,1-dimethylethyl ester instead of 3-methyl-3-oxetanamine hydrochloride (1:1). $^1$H NMR (400 MHz, DMSO-d$_6$) δ ppm 1.05 (d, J=6.6 Hz, 3H), 1.37 (s, 9H), 1.97-2.17 (m, 2H), 2.17-2.23 (m, 3H), 2.88 (dt, J=13.4, 6.5 Hz, 1H), 2.96-3.08 (m, 1H), 3.09-3.29 (m, 5H), 3.42-3.51 (m, 1H), 6.79 (br. s., 1H), 7.00-7.11 (m, 2H), 7.34-7.42 (m, 1H), 7.50 (dd, J=6.9, 2.1 Hz, 1H), 9.99 (s, 1H). Method C; Rt: 0.99 min. m/z: 459.2 (M+H)$^+$ Exact mass: 458.2.

Compound 39: (3S)—N-(4-fluoro-3-methyl-phenyl)-1-[[(1R)-2-hydroxy-1-methyl-ethyl]sulfamoyl]pyrrolidine-3-carboxamide

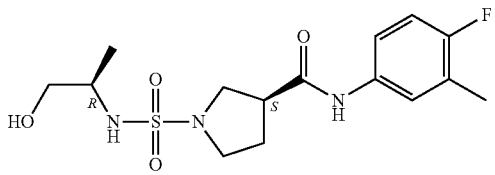

Compound 39 was prepared similarly as compound 34, using D-alaninol instead of 3-methyl-3-oxetanamine hydrochloride (1:1). $^1$H NMR (400 MHz, DMSO-d$_6$) δ ppm 1.10 (d, J=6.4 Hz, 3H), 1.98-2.18 (m, 2H), 2.20 (d, J=1.8 Hz, 3H), 3.09-3.31 (m, 6H), 3.39-3.53 (m, 2H), 4.70 (t, J=5.6 Hz, 1H), 6.98 (d, J=5.7 Hz, 1H), 7.06 (t, J=9.2 Hz, 1H), 7.34-7.44 (m, 1H), 7.51 (dd, J=7.0, 2.4 Hz, 1H), 10.00 (s, 1H). Method C; Rt: 0.75 min. m/z: 360.2 (M+H)$^+$ Exact mass: 359.1.

Compound 40: (3S)-1-[(2-cyano-1-methyl-ethyl)sulfamoyl]-N-(4-fluoro-3-methyl-phenyl)pyrrolidine-3-carboxamide

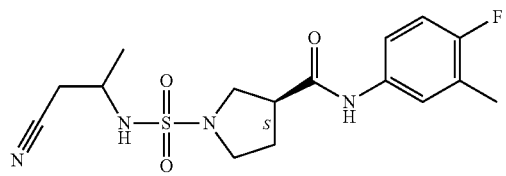

Compound 40 was prepared similarly as compound 34, using 3-aminobutanenitrile instead of 3-methyl-3-oxetanamine hydrochloride (1:1). $^1$H NMR (400 MHz, DMSO-d$_6$) δ ppm 1.23 (dd, J=6.7, 2.1 Hz, 3H), 2.00-2.12 (m, 1H), 2.12-2.19 (m, 1H), 2.20 (d, J=1.5 Hz, 3H), 2.60-2.79 (m, 2H), 3.11-3.22 (m, 1H), 3.22-3.28 (m, 1H), 3.28-3.38 (m, 2H), 3.45-3.54 (m, 1H), 3.54-3.66 (m, 1H), 7.06 (t, J=9.1 Hz, 1H), 7.36-7.43 (m, 1H), 7.51 (dd, J=7.0, 2.2 Hz, 1H), 7.62 (br. s, 1H), 10.02 (s, 1H). Method C; Rt: 0.83 min. m/z: 386.3 (M+NH$_4$)$^+$ Exact mass: 368.1.

Compound 41: trans-N-(4-fluoro-3-methyl-phenyl)-1-(isopropylsulfamoyl)-4-methyl-pyrrolidine-3-carboxamide

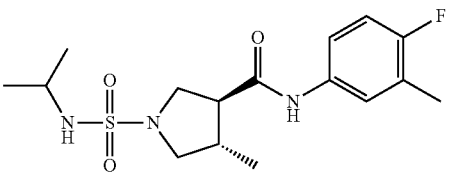 [SMILES: Cc1cc(NC(=O)[C@@H]2CN(S(=O)(=O)NC(C)C)C[C@H]2C)ccc1F]

Methyl crotonate (3.7 g, 15.6 mmol) is dissolved in DCM (50 ml) and combined with TFA (200 µl, 0.79 mmol). Then a solution of N-methoxymethyl-N-trimethylsilylmethyl-benzylamine (1.56 g, 15.6 mmol) in DCM (10 ml) is added drop wise within 20 minutes. The reaction mixture was stirred for 16 and then concentrated in vacuum. The residue was used as such in the next step. The crude mentioned above was dissolved in THF (40 mL) and combined with a solution of lithium hydroxide (3.74 g, 156 mmol) in water (10 mL). The mixture was stirred for 24 hours at room temperature. The reaction mixture was evaporated to dryness and water was removed with toluene (2×50 mL). The residue was used as such in the next step.

The crude mentioned above was dissolved in DMF (30 mL). Triethylamine hydrochloride (25.77 g, 187 mmol), triethylamine (6.51 mL, 46.8 mmol) and HATU were added followed by 4-fluoro-3-methyl-aniline (2.54 g, 20.3 mmol). The reaction mixture was stirred at RT for 1 hour. The reaction mixture was filtered under nitrogen atmosphere and diluted with water (200 mL). The solids were filtered and washed with water to afford a brown sticky solid. The organics in the filtrate were extracted with diethyl ether. The combined organic layers were combined with the brown sticky solid and washed with brine and evaporated to dryness. The residue was purified using silica gel column chromatography (ethyl acetate in heptane from 0 to 100%) to afford (3S,4S)-1-benzyl-N-(4-fluoro-3-methyl-phenyl)-4-methyl-pyrrolidine-3-carboxamide as a brown oil (1400 mg). Method C; Rt: 1.06 min. m/z: 327.2 (M+H)$^+$ Exact mass: 326.1. This was used as such in the next step.

(3S,4S)-1-benzyl-N-(4-fluoro-3-methyl-phenyl)-4-methyl-pyrrolidine-3-carboxamide (1.40 g, 2.83 mmol) was dissolved in MeOH (50 mL) and 10% Pd on charcoal (3.01 g) was added. This mixture was hydrogenated at room temperature at a H2 pressure of 1 atm for 90 minutes. The solids were filtered off and the filtrate was evaporated under reduced pressure to afford (3S,4S)—N-(4-fluoro-3-methyl-phenyl)-4-methyl-pyrrolidine-3-carboxamide (547 mg) as a colorless oil (547 mg).

(3S,4S)—N-(4-fluoro-3-methyl-phenyl)-4-methyl-pyrrolidine-3-carboxamide (274 mg, 1.16 mmol), (2-hydroxyphenyl) N-isopropylsulfamate (349 mg, 1.51 mmol) and triethylamine (0.48 mL, 3.48 mmol) were dissolved in ACN (3 mL) and heated in the microwave for 10 minutes at 100° C. The volatiles were removed under reduced pressure and the residue was purified using prep. LCMS. (Hypersyl C18 BDS-3 µm, 100×4.6 mm), mobile phase (NH$_4$HCO$_3$ 0.2% in water, methanol). The desired fractions were combined and evaporated to dryness, dissolved in methanol again and evaporated to dryness to afford a crude which was repurified using prep. LCMS. (Hypersyl C18 BDS-3 µm, 100×4.6 mm), mobile phase ($NH_4HCO_3$ 0.2% in water, acetonitrile). The desired fractions were combined and evaporated to dryness, dissolved in methanol again and evaporated to dryness and dried in a vacuum oven overnight to afford compound 41 (TRANS-isomer). $^1$H NMR (600 MHz, DMSO-$d_6$) δ ppm 1.04 (d, J=6.6 Hz, 3H), 1.12 (dd, J=6.5, 2.1 Hz, 6H), 2.20 (d, J=1.8 Hz, 3H), 2.41-2.48 (m, 1H), 2.71 (q, J=9.1 Hz, 1H), 2.80 (t, J=9.4 Hz, 1H), 3.25 (t, J=9.4 Hz, 1H), 3.39 (sxt, J=6.3 Hz, 1H), 3.45 (dd, J=9.5, 7.5 Hz, 1H), 3.52 (dd, J=9.7, 8.2 Hz, 1H), 7.07 (t, J=9.2 Hz, 2H), 7.40 (ddd, J=8.6, 4.5, 2.8 Hz, 1H), 7.53 (dd, J=7.0, 2.2 Hz, 1H), 10.05 (s, 1H). Method E; Rt: 1.73 min. m/z: 358.4 (M+H)$^+$ Exact mass: 357.1.

Compound 42: 3-fluoro-N-(4-fluoro-3-methyl-phenyl)-1-[[(3S)-tetrahydrofuran-3-yl]sulfamoyl]pyrrolidine-3-carboxamide

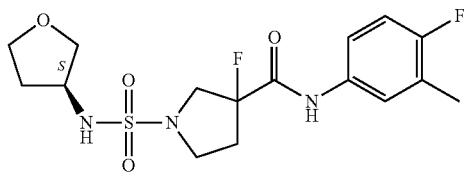

(S)-(−)-3-aminotetrahydrofuran p-toluenesulfonate (5.0 g, 19.3 mmol) was added to a stirred mixture of 1,3,2-benzodioxathiole 2,2-dioxide (4.26 g, 19.3 mmol) and triethylamine (5.36 mL, 38.6 mmol) in ACN (50 mL). The reaction mixture was stirred for 18 hours. The reaction mixture was evaporated to dryness at 25° C. to afford a residue which was purified using silica gel column chromatography (ethyl acetate in heptane from 20 to 60%) to afford (2-hydroxyphenyl) N-[(3S)-tetrahydrofuran-3-yl]sulfamate as a slightly green sticky oil (2.4 g). $^1$H NMR (400 MHz, DMSO-$d_6$) δ ppm 1.77-1.93 (m, 1H), 2.02-2.20 (m, 1H), 3.57 (dd, J=9.1, 4.1 Hz, 1H), 3.66 (td, J=8.2, 5.6 Hz, 1H), 3.70-3.80 (m, 2H), 4.02-4.23 (m, 1H), 6.78-6.84 (m, 1H), 6.96 (dd, J=8.1, 1.5 Hz, 1H), 7.07-7.15 (m, 1H), 7.23 (dd, 1.5 Hz, 1H), 8.46 (d, J=5.5 Hz, 1H), 9.85 (s, 1H).

3-fluoro-N-(4-fluoro-3-methyl-phenyl)pyrrolidine-3-carboxamide (400 mg, 1.57 mmol), (2-hydroxyphenyl) N-[(3S)-tetrahydrofuran-3-yl]sulfamate (487 mg, 1.88 mmol) and triethylamine (0.44 mL, 3.13 mmol) were dissolved in ACN (5 mL) and heated in the microwave for 10 minutes at 100° C. The volatiles were removed under reduced pressure. The residue was dissolved in DCM (20 mL) and washed with aqueous HCl (1 M) (2×5 mL) and brine (5 mL). The organic layer was concentrated to dryness and the residue was purified using silica gel chromatography (ethyl acetate in heptane from 5 to 100%) yielding compound 42 as a sticky oil (361 mg). $^1$H NMR (400 MHz, DMSO-$d_6$) δ ppm 1.73-1.90 (m, 1H), 2.03-2.16 (m, 1H), 2.22 (s, 3H), 2.27-2.63 (m, 2H), 3.37-3.56 (m, 3H), 3.58-3.84 (m, 5H), δ 3.85-3.98 (m, 1H), 7.11 (t, J=9.1 Hz, 1H), 7.44-7.54 (m, 1H), 7.56-7.77 (m, 2H), 10.22 (br. s., 1H).

The racemic mixture 42 was separated in enantiomers by Prep SFC (Stationary phase: Chiralcel Diacel OJ 20×250 mm), mobile phase: $CO_2$, MeOH with 0.2% iPrNH$_2$). OJ-H 250 mm×4.6 mm, Flow: 5 mL/min, mobile phase: 10% MeOH (containing 0.2% iPrNH$_2$) hold 4 min. Rt: 42a: 3.66 min, 42b: 4.26 min.

Compound 43: N-(4-fluoro-3-methyl-phenyl)-3-[[(3S)-tetrahydrofuran-3-yl]sulfamoyl]-3-azabicyclo[3.1.0]hexane-1-carboxamide

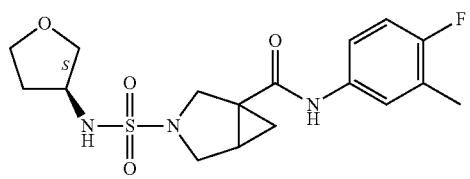

Ethyl 3-benzyl-3-azabicyclo[3.1.0]hexane-1-carboxylate (synthesis described in WO201233956A1) (1.03 g, 4.2 mmol) was dissolved in THF. Water (10 mL) and LiOH (0.50 g, 21 mmol) were added to the reaction mixture which was stirred at room temperature for 12 hours. The reaction mixture was heated at reflux for 48 hours. The reaction mixture was evaporated to dryness. Azeotropic removal of water with toluene (2×20 mL) to obtain a crude which was used as such in the next step.

The crude mentioned above was suspended in DCM (50 mL). Triethylamine hydrochloride (5.78 g, 42.0 mmol), 4-fluoro-3-methyl-aniline (788 mg, 6.3 mmol) and HATU were added. The reaction mixture was stirred at RT for 2 hours. DMF (100 mL) and 4-fluoro-3-methyl-aniline (525 mg, 4.2 mmol) were added and the reaction mixture was stirred for 72 hours. The reaction mixture was diluted with DCM (100 mL) washed with saturated aqueous sodium bicarbonate (2×50 mL), dried ($Na_2SO_4$), filtered and evaporated. The crude was purified using silica gel column chromatography (ethyl acetate in heptane from 0 to 100%) to afford 3-benzyl-N-(4-fluoro-3-methyl-phenyl)-3-azabicyclo [3.1.0]hexane-1-carboxamide (420 mg) as colorless sticky oil which was used as such in the next step. Method C; Rt: 1.17 min. m/z: 325.2 (M+H)$^+$ Exact mass: 324.1 3-benzyl-N-(4-fluoro-3-methyl-phenyl)-3-azabicyclo[3.1.0]hexane-1-carboxamide (400 mg) was dissolved in MeOH (50 mL) and 10% Pd on charcoal (262 mg) was added. This mixture was hydrogenated at room temperature at a $H_2$ pressure of 1 atm for 60 minutes. The solids were filtered off and the filtrate was evaporated under reduced pressure to afford (1S,5S)—N-(4-fluoro-3-methyl-phenyl)-3-azabicyclo [3.1.0]hexane-1-carboxamide (282 mg) as a colorless oil. Method C; Rt: 0.60 min. m/z: 235.2 (M+H)$^+$ Exact mass: 234.1.

N-(4-fluoro-3-methyl-phenyl)-3-azabicyclo[3.1.0]hexane-1-carboxamide (141 mg, 0.58 mmol), (2-hydroxyphenyl) N-[(3S)-tetrahydrofuran-3-yl]sulfamate (180 mg, 0.70 mmol) and triethylamine (0.16 mL, 1.16 mmol) were dissolved in ACN (3 mL) and heated in the microwave for 10 minutes at 100° C. The volatiles were removed under reduced pressure. The residue was dissolved in DCM (20 mL) and washed with aqueous HCl (1 M) (2×5 mL) and brine (5 mL).

The organic layer was concentrated to dryness and the residue was purified using silica gel chromatography (ethyl acetate in heptane from 30 to 100%) yielding compound 43 as a sticky oil (138 mg). $^1$H NMR (400 MHz, DMSO-$d_6$) δ ppm 1.03 (t, J=4.6 Hz, 1H), 1.41 (dd, J=8.1, 4.8 Hz, 1H), 1.76-1.86 (m, 1H), 2.03-2.14 (m, 1H), 2.17 (ddd, 5.0, 3.4 Hz, 1H), 2.20 (d, J=1.6 Hz, 3H), 3.27-3.38 (m, 2H), 3.50 (dd, J=8.9, 4.4 Hz, 1H), 3.56 (dd, J=9.3, 2.8 Hz, 1H), 3.62-3.66 (m, 1H), 3.64-3.69 (m, 1H), 3.73-3.80 (m, 2H), 3.81-3.89 (m, 1H), 7.05 (t, J=9.3 Hz, 1H), 7.42 (ddd, J=8.7, 4.6, 2.8 Hz, 1H), 7.50 (dd, J=7.3, 2.4 Hz, 1H), 9.30 (s, 1H). Method C; Rt: 0.83 min. m/z: 401.3 (M+NH$_4$)$^+$ Exact mass: 383.1.

Compound 44: (3S)—N-(3,4-difluorophenyl)-1-[(3-methyloxetan-3-yl)sulfamoyl]pyrrolidine-3-carboxamide

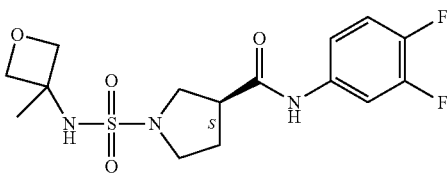

(3S)—N-(3,4-difluorophenyl)pyrrolidine-3-carboxamide hydrochloride was prepared similarly as (3S)—N-(4-fluoro-3-methyl-phenyl)pyrrolidine-3-carboxamide hydrochloride using 3,4-difluoroaniline instead of 4-fluoro-3-methylaniline. Compound 44 was prepared similarly as compound 34. $^1$H NMR (400 MHz, DMSO-d$_6$) δ ppm 1.60 (s, 3H), 2.00-2.22 (m, 2H), 3.11-3.30 (m, 4H), 3.49 (dd, J=9.6, 8.0 Hz, 1H), 4.21 (d, J=6.4 Hz, 2H), 4.65 (d, J=5.9 Hz, 2H), 7.25-7.33 (m, 1H), 7.38 (dt, J=10.5, 9.1 Hz, 1H), 7.63 (s, 1H), 7.78 (ddd, J=13.3, 7.5, 2.5 Hz, 1H), 10.28 (s, 1H). Method C; Rt: 0.78 min. m/z: 393.1 (M+NH$_4$)$^+$ Exact mass: 375.1.

Compound 45: (3S)—N-(3,4-difluorophenyl)-1-[[(1R)-1-methylpropyl]sulfamoyl]pyrrolidine-3-carboxamide

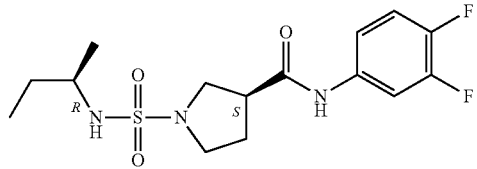

(3S)—N-(3,4-difluorophenyl)pyrrolidine-3-carboxamide hydrochloride was prepared similarly as (3S)—N-(4-fluoro-3-methyl-phenyl)pyrrolidine-3-carboxamide hydrochloride using 3,4-difluoroaniline instead of 4-fluoro-3-methylaniline. Compound 45 was prepared similarly as compound 34 using (R)-(−)-2-aminobutane instead of 3-methyl-3-oxetanamine hydrochloride (1:1). $^1$H NMR (400 MHz, DMSO-d$_6$) δ ppm 0.86 (t, J=7.5 Hz, 3H), 1.10 (d, J=6.6 Hz, 3H), 1.31-1.51 (m, 2H), 1.98-2.21 (m, 2H), 3.10-3.29 (m, 5H), 3.47 (dd, J=9.6, 8.0 Hz, 1H), 7.02 (d, J=8.1 Hz, 1H), 7.24-7.32 (m, 1H), 7.38 (dt, J=10.6, 9.1 Hz, 1H), 7.78 (ddd, J=13.3, 7.5, 2.5 Hz, 1H), 10.26 (s, 1H). Method C; Rt: 0.95 min. m/z: 362.2 (M+H)$^+$ Exact mass: 361.1.

Compound 46: (3S)—N-(3,4-difluorophenyl)-1-[[(3S)-tetrahydrofuran-3-yl]sulfamoyl]pyrrolidine-3-carboxamide

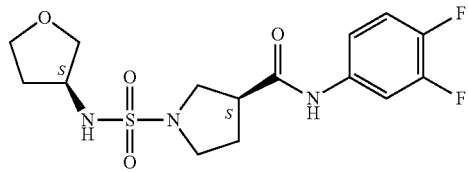

(3S)—N-(3,4-difluorophenyl)pyrrolidine-3-carboxamide hydrochloride was prepared similarly as (3S)—N-(4-fluoro-3-methyl-phenyl)pyrrolidine-3-carboxamide hydrochloride using 3,4-difluoroaniline instead of 4-fluoro-3-methylaniline. Compound 46 was prepared similarly as compound 34 using (S)-(−)-3-aminotetrahydrofuran-4-toluene-sulfonate instead of 3-methyl-3-oxetanamine hydrochloride (1:1). $^1$H NMR (400 MHz, DMSO-d$_6$) δ ppm 1.75-1.86 (m, 1H), 2.01-2.12 (m, 2H), 2.12-2.22 (m, 1H), 3.12-3.30 (m, 4H), 3.44-3.54 (m, 2H), 3.65 (td, J=8.0, 5.9 Hz, 1H), 3.71-3.81 (m, 2H), 3.81-3.92 (m, 1H), 7.24-7.33 (m, 1H), 7.38 (dt, J=10.6, 9.0 Hz, 1H), 7.47 (br. s., 1H), 7.78 (ddd, J=13.3, 7.5, 2.5 Hz, 1H), 10.28 (br. s., 1H). Method C; Rt: 0.80 min. m/z: 376.0 (M+H)$^+$ Exact mass: 375.1.

Compound 47: (3S)—N-(4-fluoro-3-methyl-phenyl)-1-[[3-(2-hydroxyethyl)oxetan-3-yl]sulfamoyl]pyrrolidine-3-carboxamide

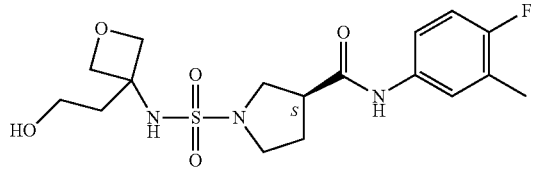

Compound 47 was prepared similarly as compound 34 using 2-(3-aminooxetan-3-yl)ethanol instead of 3-methyl-3-oxetanamine hydrochloride (1:1). $^1$H NMR (400 MHz, DMSO-d$_6$) δ ppm 2.01-2.18 (m, 4H), 2.20 (d, J=1.8 Hz, 3H), 3.10-3.30 (m, 4H), 3.51 (dd, J=9.5, 8.1 Hz, 1H), 3.56-3.64 (m, 2H), 4.39 (d, J=6.6 Hz, 2H), 4.47 (t, J=5.1 Hz, 1H), 4.64 (d, J=6.4 Hz, 2H), 7.07 (t, J=9.2 Hz, 1H), 7.36-7.43 (m, 1H), 7.48-7.55 (m, 2H), 10.02 (s, 1H). Method C; Rt: 0.72 min. m/z: 402.1 (M+H)$^+$ Exact mass: 401.1.

Compound 48: (3S)—N-(4-fluoro-3-methyl-phenyl)-1-[(1-methyl-2-oxo-pyrrolidin-3-yl)sulfamoyl]pyrrolidine-3-carboxamide

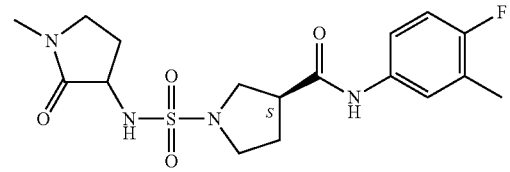

Compound 48 was prepared similarly as compound 34 using 3-amino-1-methyl-2-pyrrolidinone instead of 3-methyl-3-oxetanamine hydrochloride (1:1). ¹H NMR (400 MHz, DMSO-d₆) δ ppm 1.71-1.85 (m, 1H), 2.00-2.10 (m, 1H), 2.10-2.18 (m, 1H), 2.20 (d, J=1.8 Hz, 3H), 2.29-2.40 (m, 1H), 2.74 (s, 3H), 3.12-3.30 (m, 5H), 3.33-3.41 (m, 1H), 3.55 (td, J=8.7, 3.9 Hz, 1H), 3.98 (qd, J=9.1, 5.8 Hz, 1H), 7.06 (t, J=9.1 Hz, 1H), 7.35-7.43 (m, 1H), 7.52 (d, J=7.0 Hz, 1H), 7.56 (dd, J=13.8, 8.9 Hz, 1H), 9.99 (d, J=7.5 Hz, 1H). Method C; Rt: 0.75 min. m/z: 399.2 (M+H)⁺ Exact mass: 398.1.

Compound 49: (3S)—N-(4-fluoro-3-methyl-phenyl)-1-(6-oxa-2-azaspiro[3.3]heptan-2-ylsulfonyl)pyrrolidine-3-carboxamide

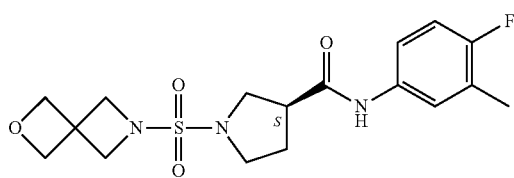

Compound 49 was prepared similarly as compound 34 using 2-oxa-6-azaspiro[3.3]heptane instead of 3-methyl-3-oxetanamine hydrochloride (1:1). ¹H NMR (400 MHz, DMSO-d₆) δ ppm 1.99-2.18 (m, 2H), 2.20 (d, J=1.5 Hz, 3H), 3.09-3.21 (m, 2H), 3.22-3.30 (m, 1H), 3.33-3.40 (m, 1H), 3.51 (dd, J=9.7, 7.9 Hz, 1H), 4.00 (s, 4H), 4.65 (s, 4H), 7.07 (t, J=9.2 Hz, 1H), 7.35-7.44 (m, 1H), 7.51 (dd, J=7.0, 2.4 Hz, 1H), 10.02 (s, 1H). Method C; Rt: 0.81 min. m/z: 384.1 (M+H)⁺ Exact mass: 383.1.

Compound 50: (3S)—N-(4-fluoro-3-methyl-phenyl)-1-[(1-methyl-5-oxo-pyrrolidin-3-yl)sulfamoyl]pyrrolidine-3-carboxamide

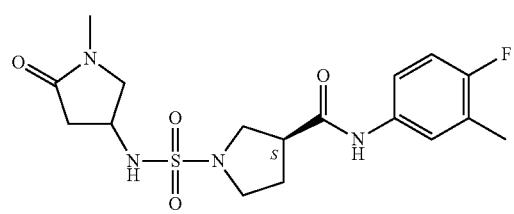

Compound 50 was prepared similarly as compound 34 using 4-amino-1-methyl-pyrrolidin-2-one hydrochloride instead of 3-methyl-3-oxetanamine hydrochloride (1:1). ¹H NMR (400 MHz, DMSO-d₆) δ ppm 2.00-2.11 (m, 1H), 2.11-2.19 (m, 1H), 2.20 (d, J=1.8 Hz, 3H), 2.23 (d, J=5.5 Hz, 1H), 2.56 (dd, J=16.8, 8.5 Hz, 1H), 2.69 (d, J=4.2 Hz, 3H), 3.10-3.20 (m, 1H), 3.20-3.26 (m, 2H), 3.26-3.30 (m, 2H), 3.43-3.52 (m, 1H), 3.55-3.64 (m, 1H), 3.90-4.02 (m, 1H), 7.07 (t, J=9.1 Hz, 1H), 7.33-7.44 (m, 1H), 7.51 (d, J=7.0, 2.6 Hz, 1H), 7.63 (dd, J=7.0, 3.1 Hz, 1H), 10.01 (d, J=2.6 Hz, 1H). Method C; Rt: 0.72 min. m/z: 399.2 (M+H)⁺ Exact mass: 398.1.

Compound 51: methyl N-[(2R)-2-[[(3S)-3-[(4-fluoro-3-methyl-phenyl)carbamoyl]pyrrolidin-1-yl]sulfonylamino]propyl]carbamate

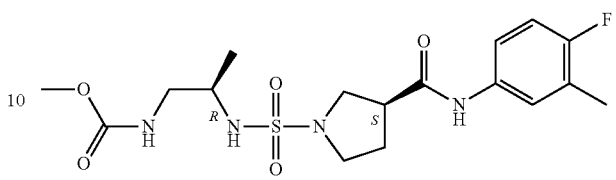

tert-butyl N-[(2R)-2-[[(3S)-3-[(4-fluoro-3-methyl-phenyl)carbamoyl]pyrrolidin-1-yl]sulfonylamino]propyl]carbamate was prepared similarly as compound 34 using N-[(2R)-2-aminopropyl]-carbamic acid 1,1-dimethylethyl ester instead of 3-methyl-3-oxetanamine hydrochloride (1:1).

tert-butyl N-[(2R)-2-[[(3S)-3-[(4-fluoro-3-methyl-phenyl)carbamoyl]pyrrolidin-1-yl]sulfonylamino]propyl]carbamate (2.07 g, 4.52 mmol) was dissolved in DCM (25 mL). HCl (6M in iPrOH) (25 mL) was added and the reaction mixture was stirred overnight at room temperature. The volatiles were removed under reduced pressure and the residue was used as such in the next step.

The crude mentioned above was dissolved in DCM (20 mL) together with DIPEA (3.11 mL, 18.1 mmol). Methyl chloroformate (0.52 mL, 6.77 mmol) was added drop wise and the reaction mixture was stirred overnight at room temperature. The volatiles were removed under reduced pressure and the residue was purified on silica using a heptane to EtOAc gradient yielding the product as an oil which solidified on standing to a white powder (394 mg). ¹H NMR (400 MHz, DMSO-d₆) δ ppm 1.07 (d, J=6.6 Hz, 3H), 1.99-2.18 (m, 2H), 2.20 (d, J=1.8 Hz, 3H), 2.93 (dt, J=13.5, 6.8 Hz, 1H), 3.02-3.30 (m, 5H), 3.32 (s, 3H), 3.34-3.39 (m, 1H), 3.48 (dd, J=9.5, 8.4 Hz, 1H), 7.02-7.10 (m, 2H), 7.12 (t, J=5.9 Hz, 1H), 7.35-7.42 (m, 1H), 7.51 (dd, 2.4 Hz, 1H), 10.00 (s, 1H). Method C; Rt: 0.81 min. m/z: 417.1 (M+H)⁺ Exact mass: 416.2. [α]_D²⁰: −12.9° (c 0.52 w/v %, DMF).

Biological Examples—Anti-HBV Activity of Compounds of Formula (I)

The anti-HBV activity was measured using a stable transfected cell line, HepG2.2.15. This cell line was described to secrete relatively consistent high levels of HBV virion particles, which have been shown to cause both acute and chronic infection and disease in chimpanzees.

For the antiviral, assay cells were treated twice for three days with serially diluted compound in 96-well plates in duplicate. After 6 days of treatment the antiviral activity was determined by quantification of purified HBV DNA from secreted virions using realtime PCR and an HBV specific primer set and probe.

The anti HBV activity was also measured using the HepG2.117 cell line, a stable, inducibly HBV producing cell line, which replicates HBV in the absence of doxicycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was tested using HepG2 cells, incubated for 4 days in the presence of compounds. The viability of the cells was assessed using a Resazurin assay. Results are displayed in Table 1.

TABLE 1

| Co. No. | HepG2 2.15 EC50 (μM) | HepG2 117 EC50 (μM) | HepG2 4 days CC50 (μM) |
|---|---|---|---|
| 1 | 0.94 | 0.72 | >25 |
| 2 | 1.32 | 0.31 | >25 |
| 3 | >25 | 1.49 | >25 |
| 4 | 16.4 | 10.7 | >25 |
| 5 | 9.1 | 2.0 | >25 |
| 6 | 1.9 | 0.62 | >25 |
| 7 | 13.5 | 4.7 | >25 |
| 8 | 0.58 | 0.33 | >25 |
| 9 | 1.4 | 0.95 | >25 |
| 10 | 4.3 | 0.76 | 22.9 |
| 11 | 7.0 | 3.1 | >25 |
| 12 | 4.1 | 2.3 | >25 |
| 13 | 4.6 | 3.4 | >25 |
| 14 | 1.9 | 1.5 | >25 |
| 15 | 12.5 | 14.7 | >25 |
| 16 | 3.5 | 2.5 | >25 |
| 17 | 5.9 | 5.9 | >25 |
| 18 | 5.8 | 5.3 | >25 |
| 19 | 8.4 | 2.9 | >25 |
| 20 | 16.1 | 4.0 | >25 |
| 21 | 5.4 | 2.7 | >25 |
| 22 | 13.6 | 8.6 | >25 |
| 23 | 0.96 | 1.4 | >25 |
| 24 | 0.50 | 0.33 | >25 |
| 24a | 1.4 | 1.7 | >25 |
| 24b | 0.11 | 0.061 | >25 |
| 25 | 5.5 | 0.43 | >25 |
| 26 | 4.4 | 0.41 | >25 |
| 27 | 2.8 | 2.0 | >25 |
| 28 | 2.0 | 3.9 | >25 |
| 29 | 13.7 | 18.9 | >25 |
| 29a | >25 | >25 | >25 |
| 29b | 18.3 | 6.9 | >25 |
| 30 | 0.61 | 4.7 | >25 |
| 31 | 0.45 | 0.47 | >25 |
| 32 | 0.18 | 0.12 | >25 |
| 33 | 0.15 | 0.075 | >25 |
| 34 | 0.11 | 0.11 | >25 |
| 35a | 0.563 | 0.228 | >25 |
| 35b | >5 | >5 | >25 |
| 36a | 2.39 | 2.65 | >25 |
| 36b | 0.46 | 0.38 | >25 |
| 37 | 0.27 | 0.53 | >25 |
| 38 | 3.65 | 2.07 | >25 |
| 39 |  | 0.15 | >25 |
| 40 | 0.29 | 0.12 | >25 |
| 41 | 0.53 | 0.42 | >25 |
| 42a | >5 | >5 | >25 |
| 42b | 3.25 | 1.69 | >25 |
| 43 | 0.58 | 0.85 | >25 |
| 44 | 0.61 | 0.42 | >25 |
| 45 | 3.25 | 0.54 | >25 |
| 46 | 0.60 | 0.24 | >25 |
| 47 | 0.065 | 0.091 | >25 |
| 48 | 1.37 | 0.57 | >25 |
| 49 | 1.49 | 0.95 | >25 |
| 50 | 0.35 | 0.46 | >25 |
| 51 | 0.15 | 0.057 | >25 |
| 52 | 0.55 | 0.46 | >25 |

The invention claimed is:
1. A method of producing a compound of Formula I, said method comprising
reacting a compound of Formula II with a compound of $R^4$—X—Y to form a compound of Formula III, and
reacting the compound of Formula III with an aniline of Formula IV

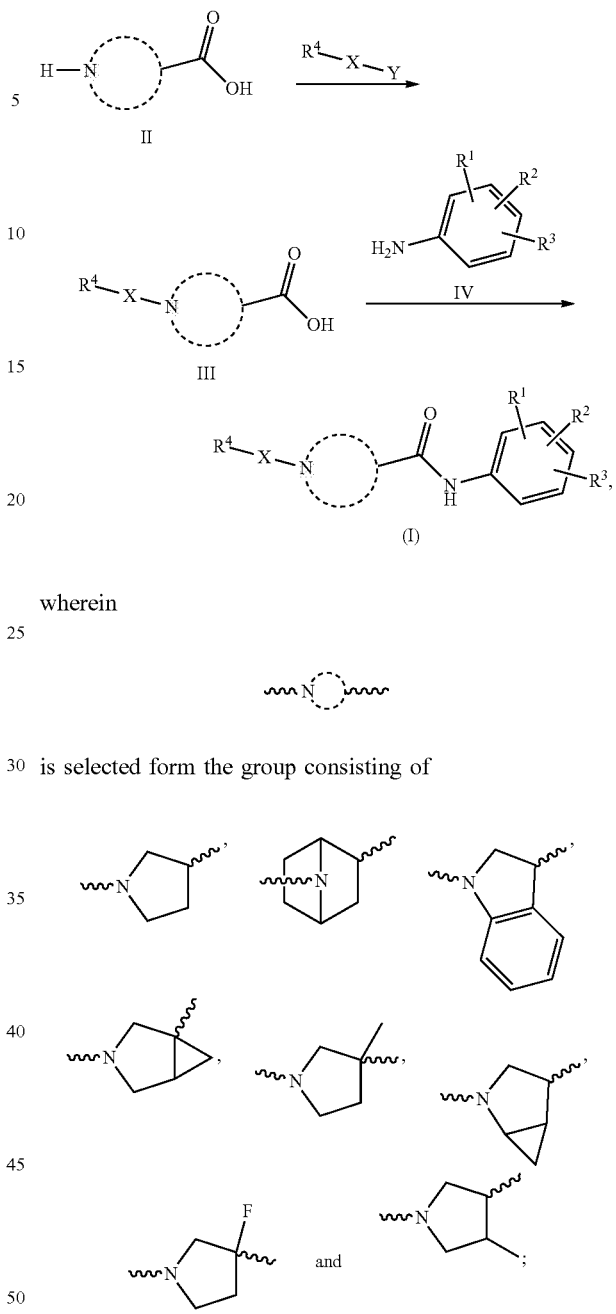

wherein is selected form the group consisting of

X is —(SO$_2$)—, and $R^4$ is selected from the group consisting of —NR$^5$R$^6$, $C_1$-$C_6$alkyl, and a 3-7 membered saturated ring optionally containing one or more heteroatoms each independently selected from the group consisting of O, S and N, said 3-7 membered saturated ring or $C_1$-$C_6$alkyl optionally substituted with one or more substituents each independently selected from the group consisting of hydrogen, fluoro, $C_1$-$C_4$alkyloxy, OH, oxo, $C_1$-$C_4$alkyl, and cyclopropyl; or
X is a single bond, and $R^4$ is —C(=O)OR$^7$;
Y is chloro;
$R^1$, $R^2$ and $R^3$ are each independently selected from the group consisting of hydrogen, halogen, CN, CHF$_2$, CH$_2$F, CF$_3$, $C_1$-$C_3$alkyl and cyclopropyl;

$R^5$ is hydrogen or methyl;

$R^6$ is $C_1$-$C_6$alkyl or a 3-7 membered saturated ring optionally containing one or more heteroatoms each independently selected from the group consisting of O, S and N, said 3-7 membered saturated ring and $C_1$-$C_6$alkyl each independently optionally substituted with one or more substituents selected from the group consisting of hydrogen, fluoro, CN, OH, oxo, —NHC(=O)O—$C_1$-$C_4$alkyl, and $C_1$-$C_4$alkyl optionally substituted with one or more substituents selected from the group consisting of $R^8$, fluoro, $C_1$-$C_4$alkyloxy,

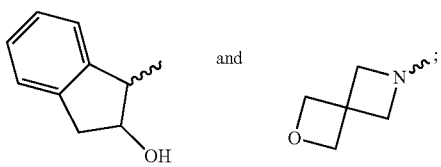

and $R^7$ is $C_1$-$C_6$alkyl or a 3-7 membered saturated ring optionally containing one or more heteroatoms each independently selected from the group consisting of O, S and N; and $R^8$ is selected from the group consisting hydrogen, OH, $C_1$-$C_4$alkyl and CN.

2. The method of claim 1, wherein the compound of formula $R_4$—X—Y is selected from the group consisting of methanesulfonyl chloride, cyclopropanesulfonyl chloride, 1-propanesulfonyl chloride, isopropylsulfonyl chloride, cyclopropylmethanesulfonyl chloride, tetrahydro-2H-pyran-4-sulfonyl chloride, cyclopentanesulfonyl chloride, N-isopropyl-N-methyl-sulfamoyl chloride, tetrahydro-3-furansulfonyl chloride, 1,1-dioxothiolane-3-sulfonyl chloride, 2-methoxy-ethanesulfonyl chloride, 4-hydroxy-1,1-dioxothiolane-3-sulfonyl chloride, 2-hydroxycyclohexanesulfonyl chloride, 4-methylpentane-2-sulfonyl chloride, 1-methoxypropane-2-sulfonyl chloride, pentane-3-sulfonyl chloride, (2,5-dioxopyrrolidin-1-yl) oxetan-3-yl carbonate, isopropyl chloroformate, methyl chloroformate, cyclohexanesulfonyl chloride, 2-ethyl-cyclopropanesulfonyl chloride, sec-butylsulfonyl chloride and isobutyl chloroformate.

3. The method of claim 1, wherein the compound of formula $R_4$—X—Y is selected from the group consisting of $(CH_3)_2NH_2$—$SO_2Cl$,

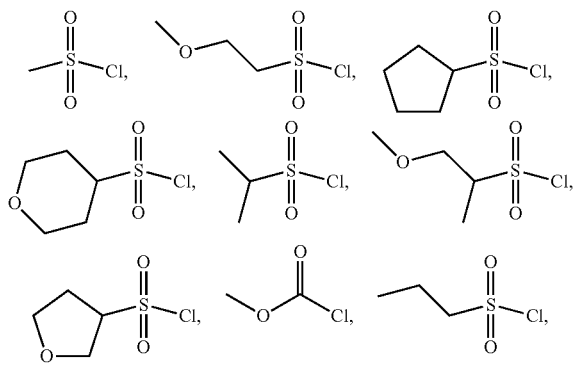

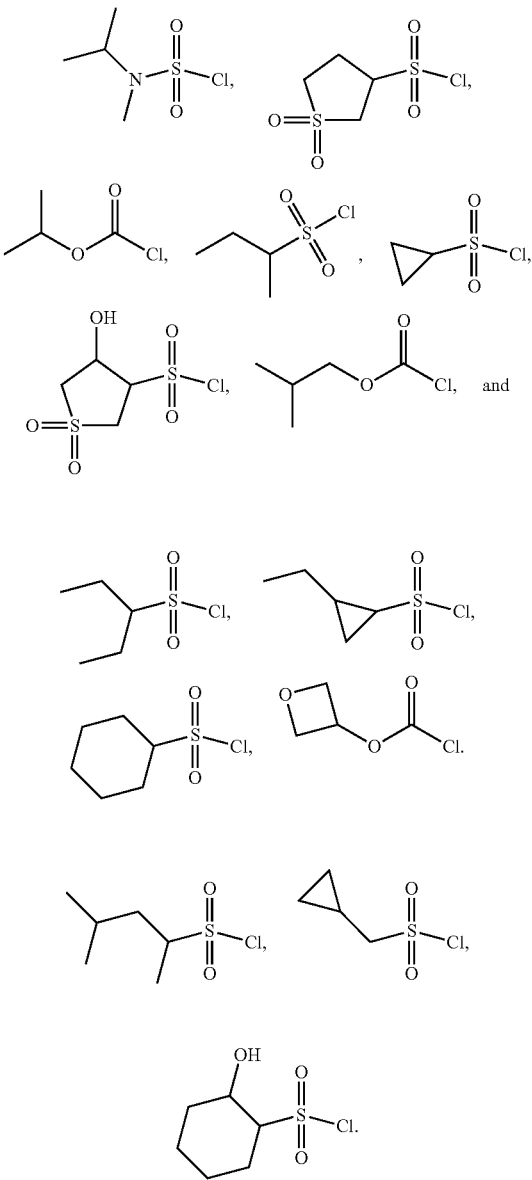

4. The method of claim 1, wherein reacting a compound of Formula II with a compound of formula $R_4$—X—Y is performed in the presence of a base.

5. The method of claim 4, wherein the base is N, N-diisopropylethylene.

6. The method of claim 1, wherein reacting the compound of Formula III with an aniline of Formula IV is performed in the presence of HATU and DIPEA in $CH_2Cl_2$.

7. A method of producing a compound of Formula I, said method comprising reacting a compound of Formula V with an aniline compound of Formula IV to form a compound of Formula VI;

deprotecting the compound of Formula VI to form a compound of Formula VII; and reacting a compound of Formula VII with a compound of formula $R_4$—X—Y

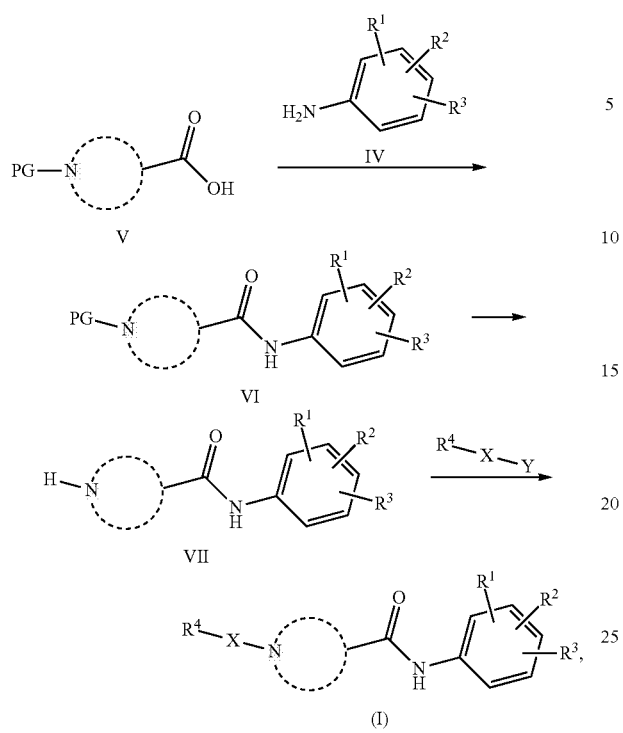

wherein
PG is a protecting group;

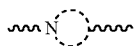

is selected form the group consisting of

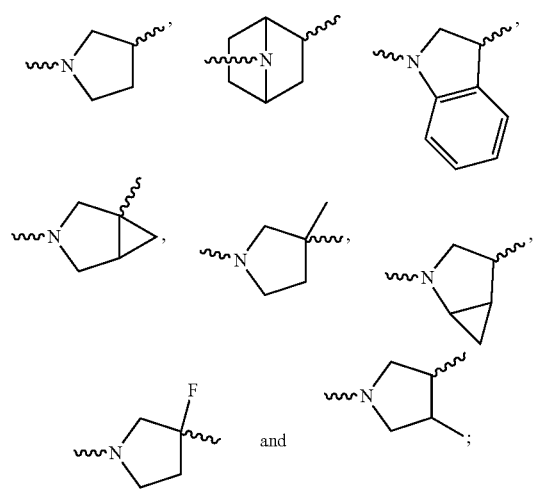

X is —(SO$_2$)—, and R$^4$ is selected from the group consisting of —NR$^5$R$^6$, C$_1$-C$_6$alkyl, and a 3-7 membered saturated ring optionally containing one or more heteroatoms each independently selected from the group consisting of O, S and N, said 3-7 membered saturated ring or C$_1$-C$_6$alkyl optionally substituted with one or more substituents each independently selected from the group consisting of hydrogen, fluoro, C$_1$-C$_4$alkyloxy, OH, oxo, C$_1$-C$_4$alkyl, and cyclopropyl; or X is a single bond, and R$^4$ is —C(=O)OR$^7$;

Y is chloro;

R$^1$, R$^2$ and R$^3$ are each independently selected from the group consisting of hydrogen, halogen, CN, CHF$_2$, CH$_2$F, CF$_3$, C$_1$-C$_3$alkyl and cyclopropyl;

R$^5$ is hydrogen or methyl;

R$^6$ is C$_1$-C$_6$alkyl or a 3-7 membered saturated ring optionally containing one or more heteroatoms each independently selected from the group consisting of O, S and N, said 3-7 membered saturated ring and C$_1$-C$_6$alkyl each independently optionally substituted with one or more substituents selected from the group consisting of hydrogen, fluoro, CN, OH, oxo, —NHC(=O)O—C$_1$-C$_4$alkyl, and C$_1$-C$_4$alkyl optionally substituted with one or more substituents selected from the group consisting of R$^8$, fluoro, C$_1$-C$_4$alkyloxy,

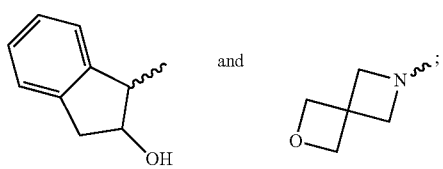

R$^7$ is C$_1$-C$_6$alkyl or a 3-7 membered saturated ring optionally containing one or more heteroatoms each independently selected from the group consisting of O, S and N; and R$^8$ is selected from the group consisting hydrogen, OH, C$_1$-C$_4$alkyl and CN.

8. The method of claim 7, wherein PG is (tert-butoxy)carbonyl or benzyloxycarbonyl.

9. The method of claim 7, wherein the compound of formula R$_4$—X—Y is selected from the group consisting of methanesulfonyl chloride, cyclopropanesulfonyl chloride, 1-propanesulfonyl chloride, isopropylsulfonyl chloride, cyclopropylmethanesulfonyl chloride, tetrahydro-2H-pyran-4-sulfonyl chloride, cyclopentanesulfonyl chloride, N-isopropyl-N-methyl-sulfamoyl chloride, tetrahydro-3-furansulfonyl chloride, 1,1-dioxothiolane-3-sulfonyl chloride, 2-methoxy-ethanesulfonyl chloride, 4-hydroxy-1,1-dioxothiolane-3-sulfonyl chloride, 2-hydroxycyclohexanesulfonyl chloride, 4-methylpentane-2-sulfonyl chloride, 1-methoxypropane-2-sulfonyl chloride, pentane-3-sulfonyl chloride, (2,5-dioxopyrrolidin-1-yl) oxetan-3-yl carbonate, isopropyl chloroformate, methyl chloroformate, cyclohexanesulfonyl chloride, 2-ethyl-cyclopropanesulfonyl chloride, sec-butylsulfonyl chloride and isobutyl chloroformate.

10. The method of claim 7, wherein the compound of formula R$_4$—X—Y is selected from the group consisting of (CH$_3$)$_2$NH$_2$—SO$_2$Cl

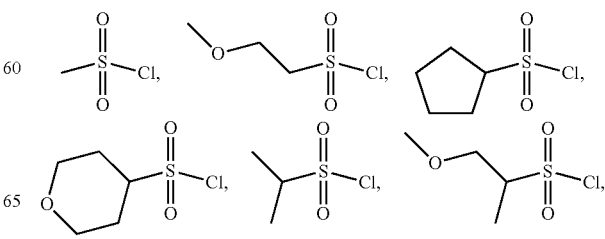

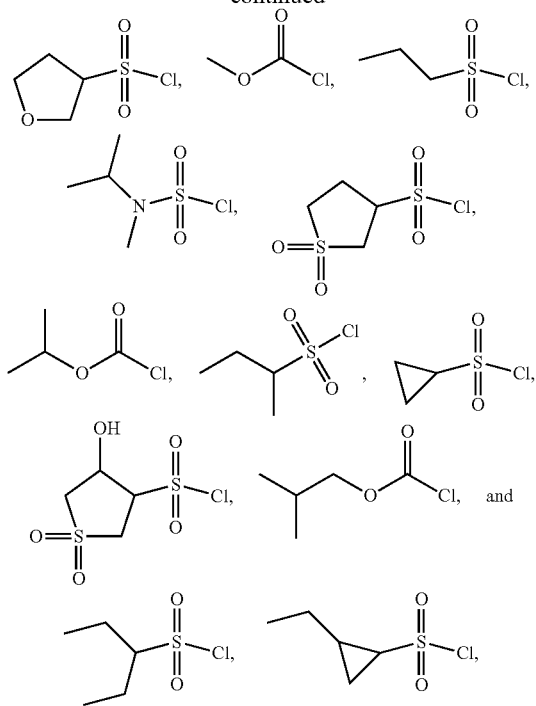
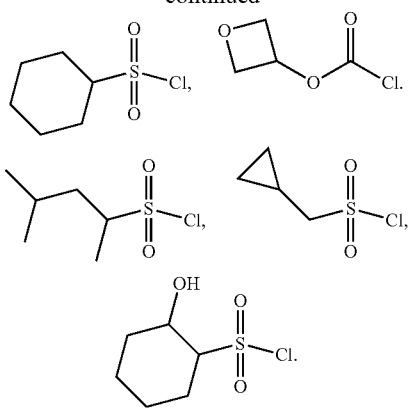
11. The method of claim 7, wherein reacting a compound of Formula VII with a compound of formula $R_4$—X—Y is performed in the presence of a base.
12. The method of claim 11, wherein the base is N,N-diisopropylethylamine.
13. The method of claim 7, wherein reacting a compound of Formula V with an aniline compound of Formula IV is performed in the presence of HATU and DIPEA in $CH_2Cl_2$.
* * * * *